(12) United States Patent
Donovan

(10) Patent No.: US 11,129,940 B2
(45) Date of Patent: Sep. 28, 2021

(54) SYRINGES, KITS, AND METHODS FOR INTRACUTANEOUS AND/OR SUBCUTANEOUS INJECTION OF PASTES

(71) Applicant: XERIS PHARMACEUTICALS, INC., Austin, TX (US)

(72) Inventor: Martin Donovan, Austin, TX (US)

(73) Assignee: Xeris Pharmaceuticals, Inc., Chicago, IL (US)

( * ) Notice: Subject to any disclaimer, the term of this patent is extended or adjusted under 35 U.S.C. 154(b) by 446 days.

(21) Appl. No.: 15/501,333

(22) PCT Filed: Aug. 6, 2015

(86) PCT No.: PCT/US2015/044060
§ 371 (c)(1),
(2) Date: Feb. 2, 2017

(87) PCT Pub. No.: WO2016/022831
PCT Pub. Date: Feb. 11, 2016

(65) Prior Publication Data
US 2017/0216529 A1    Aug. 3, 2017

Related U.S. Application Data

(60) Provisional application No. 62/034,004, filed on Aug. 6, 2014.

(51) Int. Cl.
*A61M 5/28* (2006.01)
*A61M 5/178* (2006.01)
(Continued)

(52) U.S. Cl.
CPC .......... *A61M 5/281* (2013.01); *A61K 9/0024* (2013.01); *A61K 47/14* (2013.01); *A61K 47/26* (2013.01);
(Continued)

(58) Field of Classification Search
CPC .................................................... A61K 9/0024
See application file for complete search history.

(56) References Cited

U.S. PATENT DOCUMENTS 1,929,247 A * 10/1933 Hein ....................... A61M 5/24
604/237
3,016,895 A    1/1962 Sein ............................... 604/60
(Continued)

FOREIGN PATENT DOCUMENTS

AU    2014200476 A1    2/2014
CN       1507858          6/2004
(Continued)

OTHER PUBLICATIONS

Administer Intramuscular, Subcutaneous, and Intradermal Injections, from http://www.brooksidepress.org/Products/Administer_IM_SQ_and_ID_Injections/lesson_1 . . . , pp. 1-3, published on 2007.

(Continued)

*Primary Examiner* — Nathan R Price
*Assistant Examiner* — Dung T Ulsh
(74) *Attorney, Agent, or Firm* — Sterne Kessler Goldstein & Fox

(57) ABSTRACT

This disclosure includes syringes, kits containing the same, and related methods. Some syringes are pre-loaded with paste and have a syringe body defining a reservoir having an internal first transverse dimension, a paste disposed within the reservoir, the paste having a solids concentration of greater than 50 mg/mL, a needle defining a lumen having an internal second transverse dimension that is smaller than the first transverse dimension, the needle configured to be in fluid communication with the reservoir to allow intracutaneous delivery of the paste, and a plunger and/or piston disposed within the reservoir and configured to be moved to dispense paste from the reservoir through the lumen. Some (Continued)

syringes include a fitting (e.g. Luer fitting) disposed on the syringe body and in fluid communication with the reservoir and a sealing cap disposed on the Luer fitting to seal the reservoir.

16 Claims, 9 Drawing Sheets

(51) Int. Cl.
*A61K 9/00* (2006.01)
*A61K 47/26* (2006.01)
*A61K 47/14* (2017.01)
*A61M 5/315* (2006.01)
*A61M 5/32* (2006.01)
*A61M 5/34* (2006.01)

(52) U.S. Cl.
CPC .............. *A61M 5/178* (2013.01); *A61M 5/28* (2013.01); *A61M 5/315* (2013.01); *A61M 5/329* (2013.01); *A61M 5/344* (2013.01); *A61M 2202/06* (2013.01)

(56) References Cited

U.S. PATENT DOCUMENTS

| | | | |
|---|---|---|---|
| 4,608,764 A | 9/1986 | Leuenberger | 34/295 |
| 4,848,094 A | 7/1989 | Davis et al. | 62/64 |
| 4,927,571 A | 5/1990 | Huang et al. | 264/4.3 |
| 5,031,336 A | 7/1991 | Diesner et al. | 34/287 |
| 5,092,843 A | 3/1992 | Monroe et al. | 604/138 |
| 5,208,998 A | 5/1993 | Oyler | 34/288 |
| 5,260,306 A | 11/1993 | Boardman et al. | 514/291 |
| 5,595,760 A | 1/1997 | Cherif-Cheikh | |
| 5,716,640 A | 2/1998 | Kamei et al. | 524/451 |
| 5,932,547 A | 8/1999 | Stevenson et al. | 514/10.3 |
| 5,977,082 A | 11/1999 | Gatti et al. | 514/34 |
| 6,001,336 A | 12/1999 | Gordon | 424/46 |
| 6,051,256 A | 4/2000 | Platz et al. | 424/489 |
| 6,124,261 A | 9/2000 | Stevenson et al. | 514/2.4 |
| 6,199,297 B1 | 3/2001 | Wisniewski | 34/284 |
| 6,253,463 B1 | 7/2001 | Hansen | 34/362 |
| 6,264,990 B1 | 7/2001 | Knepp et al. | 424/499 |
| 6,290,991 B1 | 9/2001 | Roser et al. | 424/502 |
| 6,309,663 B1 | 10/2001 | Patel et al. | 424/450 |
| 6,331,310 B1 | 12/2001 | Roser et al. | 424/423 |
| 6,371,939 B2 | 4/2002 | Bergens et al. | 604/156 |
| 6,495,164 B1 | 12/2002 | Ramstack et al. | 424/489 |
| 6,667,061 B2 | 12/2003 | Ramstack et al. | 424/489 |
| 6,676,958 B2 | 1/2004 | Gerber | 424/434 |
| 6,730,328 B2 | 5/2004 | Maskiewicz et al. | 424/499 |
| 7,005,421 B2 | 2/2006 | Gatti et al. | 514/34 |
| 7,163,704 B2 | 1/2007 | Zhang | 424/725 |
| 7,259,225 B2 | 8/2007 | Song et al. | 528/272 |
| 7,314,636 B2 | 1/2008 | Caseres et al. | 424/426 |
| 7,371,406 B2 | 5/2008 | Rasstack et al. | 424/489 |
| 7,396,841 B2 | 7/2008 | Doen et al. | 514/338 |
| 7,442,832 B2 | 10/2008 | Gentile et al. | 562/460 |
| 7,498,312 B2 | 3/2009 | Cohen et al. | 514/36 |
| 7,582,311 B1 | 9/2009 | Cleland et al. | 424/489 |
| 7,604,822 B2 | 10/2009 | Ionascu | 424/725.1 |
| 7,651,703 B2 | 1/2010 | Cleland et al. | 424/489 |
| 7,713,244 B1 * | 5/2010 | Cheikh | A61M 5/1782 604/218 |
| 7,915,229 B2 | 3/2011 | Cohen et al. | 514/36 |
| 8,110,209 B2 | 2/2012 | Prestrelski et al. | 424/423 |
| 9,125,805 B2 | 9/2015 | Prestrelski et al. | |
| 9,138,479 B2 | 9/2015 | Prestrelski et al. | |
| 2002/0179647 A1 | 12/2002 | Hall et al. | 222/175 |
| 2003/0026884 A1 | 2/2003 | Mantius et al. | 426/488 |
| 2003/0119825 A1 | 6/2003 | Folger et al. | 514/226.5 |
| 2003/0170289 A1 | 9/2003 | Chen et al. | 424/426 |
| 2003/0191157 A1 | 10/2003 | Doen et al. | 514/337 |
| 2004/0142043 A1 | 7/2004 | Maeda et al. | 524/499 |
| 2004/0176341 A1 | 9/2004 | Chou et al. | 514/179 |
| 2005/0019436 A1 | 1/2005 | Burch et al. | 424/760 |
| 2005/0069591 A1 | 3/2005 | Bernstein et al. | 424/489 |
| 2005/0240166 A1 | 10/2005 | Harper et al. | 604/890.1 |
| 2006/0160823 A1 | 7/2006 | Witchey-Lakshmanan et al. 514/254.07 |
| 2006/0211982 A1 * | 9/2006 | Prestrelski | A61K 38/27 604/60 |
| 2007/0196416 A1 | 8/2007 | Li et al. | 424/422 |
| 2008/0096967 A1 | 4/2008 | Lopez et al. | 514/567 |
| 2008/0132493 A1 | 6/2008 | Folger et al. | 514/224 |
| 2008/0132851 A1 * | 6/2008 | Shaw | A61M 5/31 604/199 |
| 2008/0145383 A1 | 6/2008 | Zauner et al. | 424/208.1 |
| 2008/0160067 A1 | 7/2008 | Boeckh et al. | 424/441 |
| 2008/0200383 A1 | 8/2008 | Jennings et al. | 514/11.3 |
| 2008/0220069 A1 | 9/2008 | Allison | 424/489 |
| 2008/0226689 A1 | 9/2008 | Berry et al. | 424/423 |
| 2008/0248999 A1 | 10/2008 | Steiner | 514/1.1 |
| 2008/0260840 A1 | 10/2008 | Alessi et al. | 514/12 |
| 2008/0305161 A1 | 12/2008 | Shah et al. | 424/456 |
| 2009/0143737 A1 | 6/2009 | Kobayashi et al. | 604/164.08 |
| 2009/0215883 A1 | 8/2009 | Bouzada et al. | 514/449 |
| 2009/0226530 A1 | 9/2009 | Lassner et al. | 514/1.1 |
| 2009/0233912 A1 | 9/2009 | Castile et al. | 514/220 |
| 2010/0098735 A1 | 4/2010 | Jain et al. | 424/422 |
| 2010/0120660 A1 | 5/2010 | Balschmidt et al. | 514/1.1 |
| 2011/0230569 A1 | 9/2011 | Nistor et al. | 514/777 |
| 2012/0046225 A1 | 2/2012 | Prestrelski et al. | 514/6.8 |
| 2012/0101325 A1 * | 4/2012 | Lee | A61K 9/0024 600/9 |
| 2012/0232001 A1 | 9/2012 | Prestrelski et al. | 514/5.9 |
| 2013/0123739 A1 | 5/2013 | Yoshikawa | 604/408 |
| 2013/0134188 A1 * | 5/2013 | Terakawa | A61C 5/62 222/386 |
| 2013/0317477 A1 | 11/2013 | Edwards et al. | |
| 2013/0338792 A1 * | 12/2013 | Schmieding | A61F 2/30756 623/23.73 |
| 2014/0058337 A1 | 2/2014 | Claussen et al. | 604/260 |
| 2014/0171362 A1 | 6/2014 | Prestrelski et al. | 514/5.9 |
| 2014/0171364 A1 | 6/2014 | Prestrelski et al. | |
| 2014/0179599 A1 | 6/2014 | Prestrelski et al. | 514/6.8 |
| 2014/0179600 A1 | 6/2014 | Prestrelski et al. | 514/6.8 |
| 2014/0221288 A1 | 8/2014 | Prestrelski et al. | 514/7.2 |
| 2014/0329915 A1 * | 11/2014 | Nguyen | A61L 31/041 514/774 |
| 2015/0125827 A1 * | 5/2015 | Claypool | A61C 5/50 433/226 |
| 2015/0250855 A1 | 9/2015 | Prestrelski et al. | 514/6.8 |
| 2015/0289945 A1 * | 10/2015 | Nguyen | A61F 2/12 623/23.72 |
| 2016/0151385 A1 | 6/2016 | Prestrelski et al. | 514/221 |
| 2017/0007675 A1 | 1/2017 | Prestrelski et al. | |
| 2017/0049858 A1 | 2/2017 | Prestrelski et al. | |

FOREIGN PATENT DOCUMENTS

| | | |
|---|---|---|
| CN | 101842079 | 9/2010 |
| CN | 102164579 | 8/2011 |
| CN | 103442695 | 9/2012 |
| EP | 0 916 347 | 5/1999 |
| EP | 1 502 589 | 2/2005 |
| EP | 2 060 268 | 5/2009 |
| EP | 2526996 | 11/2012 |
| GB | 2 119 248 | 11/1983 |
| JP | H07-506287 | 7/1995 |
| JP | H05-507085 | 10/1997 |
| JP | 2006-506363 | 2/2006 |
| JP | 2006-511582 | 4/2006 |
| JP | 2007-537283 | 12/2007 |
| JP | 2008-543857 | 12/2008 |
| JP | 2009-523798 | 6/2009 |
| JP | 2010-537963 | 12/2010 |
| JP | 2011-507843 | 3/2011 |
| JP | 2011-520875 | 7/2011 |
| JP | 2014-507484 | 3/2014 |
| JP | 2014-510077 | 4/2014 |
| WO | WO 1991/016882 | 11/1991 |

(56) References Cited

FOREIGN PATENT DOCUMENTS

| | | |
|---|---|---|
| WO | WO 1994/013344 | 6/1994 |
| WO | WO 1995/032730 | 12/1995 |
| WO | WO 1996/009814 | 4/1996 |
| WO | WO 1998/009613 | 3/1998 |
| WO | WO 1998/016250 | 4/1998 |
| WO | WO 1998/027963 | 7/1998 |
| WO | WO 2000/016829 | 3/2000 |
| WO | WO 2001/076682 | 10/2001 |
| WO | WO 2001/078687 | 10/2001 |
| WO | WO 2002/000137 | 1/2002 |
| WO | WO 2002/049660 | 6/2002 |
| WO | WO 2003/007782 | 1/2003 |
| WO | WO 2003/041684 | 5/2003 |
| WO | WO 2003/051398 | 6/2003 |
| WO | WO 2004/035601 | 4/2004 |
| WO | WO 2004/037242 | 5/2004 |
| WO | WO 2004/057939 | 7/2004 |
| WO | WO 2004/057959 | 7/2004 |
| WO | WO 2004/091666 | 10/2004 |
| WO | WO 2004/098643 | 11/2004 |
| WO | WO 2005/010079 | 2/2005 |
| WO | WO 2006/031376 | 3/2006 |
| WO | WO 2006/110551 | 10/2006 |
| WO | WO 2006/138347 | 12/2006 |
| WO | WO 2007/140312 | 12/2007 |
| WO | WO 2008/030469 | 3/2008 |
| WO | WO 2008/041245 | 4/2008 |
| WO | WO 2008/098212 | 8/2008 |
| WO | WO 2008/132224 | 11/2008 |
| WO | WO 2009/027697 | 3/2009 |
| WO | WO 2009/045837 | 4/2009 |
| WO | WO 2009/060473 | 5/2009 |
| WO | WO 2009/070298 | 6/2009 |
| WO | WO 2009/082437 | 7/2009 |
| WO | WO 2010/018596 | 2/2010 |
| WO | WO 2010/024209 | 3/2010 |
| WO | WO 2011/060908 | 5/2011 |
| WO | WO 2011/154725 | 12/2011 |
| WO | WO 2012/012460 | 1/2012 |
| WO | WO 2012/122535 | 9/2012 |
| WO | WO 2013/067022 | 5/2013 |
| WO | WO 2013/173687 | 11/2013 |
| WO | WO 2014/004895 | 1/2014 |
| WO | WO 2014/036323 | 3/2014 |
| WO | WO 2014/124151 | 8/2014 |
| WO | WO 2015/0120231 | 8/2015 |
| WO | WO 2015/153728 | 10/2015 |
| WO | WO 2016/022831 | 2/2016 |
| WO | WO 2016/196976 | 12/2016 |
| WO | WO 2016/201248 | 12/2016 |

OTHER PUBLICATIONS

Amylin Agonists, from http://www.globalrph.com/amylin-agonists.htm, pp. 1-5, accessed Nov. 30, 2014.
Anderson et al., "Revised estimate of the prevalence of multiple sclerosis in the United States", Ann. Neruol, 31(3):333-336, 1992.
Arnon and Aharoni, "Neurogenesis and neuroprotection in the CNS—fundamental elements in the effect of Glatiramer acetate on treatment of autoimmune neurological disorders ", Mol. Neurobiol., 36:245-253, 2007.
Autret, E. et al.: "Double-blind, randomized trial of diazepam versus placebo for prevention of recurrence of febrile seizures", The Journal of Pediatrics, vol. 117, No. 3, Sep. 1990, p. 490-494.
Bjartmar and Fox, "Pathological mechanisms and disease progression of multiple sclerosis: therapeutic implications", Drugs of Today, 38:17-29, 2002.
Bornstein et al., "A pilot trial of Cop 1 in exacerbateing remitting multiple sclerosis", New Eng. J. Med., 317:408-414,1987.
Bornstein et al., "A placebo-controlled, double-blind, randomized, two-center, pilot trial of Cop-1 in chronic progressive multiple sclerosis", Neurology, 41:533-539, 1991.
Bromberg, L. et al., "Transport of proteins dissolved in organic solvents across biomimetic membranes", Proceedings of the National Academy of Sciences 92(5):1262-1266, 1995.
Brown: "Clinicians' Guide to Diabetes Gadgets and Gizmos", Clinical Diabetes, 2008, 26, pp. 66-71.
Buffer Reference Center, from http://sigmaaldrich.com/life-science/core-bioreagents/biological-buffers/learningcenter. Accessed Jul. 3, 2013.
Carpenter, et al., "Rational Design of Stable Lyophilized Protein Formulations: Theory and Practice." pp. 1-25. 2002.
Cervera et al., "Mechanism of action of exenatide to reduce postprandial hyperglycemia in type 2 diabetes.", Am J Physiol Endocrinol Metab 294: E846-E852, 2008.
Chang and Hershenson, "Practical Approaches to Protein Formulation Development", In: Rationale Design of stable protein formulations—theory and practice, pp. 1-25, 2002.
Chang et al., "Development of stable freeze-dried formulation of recombinant human interleukin-1 receptor antagonist", Pharm. Res., 13(2):243-249, 1996.
Citric Acid, from http://www.boldsky.com/health/nutrition/2011/natural-citric-acid-sources-030811.html, pp. 1-3, accessed Nov. 26, 2014.
Comi & Filippi, "Treatment with glatiramer acetate delays conversion to clinically definiate multiple sclerosis (CDMS) in patients with clinically isolated syndromes (CIS)", Neurology, 71(2):153, 2008.
Comi et al, "Results from a phase III, one-year, randomized, double-blind, parallel-group, dosecomparison study with glatiramer acetate in relapsing-remitting multiple sclerosis", Mult. Sclerosis., 14(suppl. 1):S299-S301, 2008.
Comi et al., "European/Canadian multicener, double-blind, randomized, placebo-controlled study of the effects of glatiramer acetate on magnetic resonance imaging-measured disease activity and burden in patents with relapsing multiple sclerosis", Ann. Neurol., 49:290-297, 2001.
Compston et al., "The Story of Multiple Sclerosis" In: McAlpine's Multiple Sclerosis. London: Churchill Livingston, pp. 3-42, 2006.
Definition of analog, from http://cancerweb.ncl.ac.uk/cgi-bin/omd?query=analog, pp. 1-5, accessed Jul. 7, 2005.
Definition of mimetic, from http://www.merriam-webster.com/medical/mimetic, p. 1, accessed Jun. 26, 2014.
DeLuca, "Freeze drying of pharmaceuticals", J. Vac. Sci. Technol., 14(1):620, 1977.
Dhib-Jalbut, "Glatirmaer acetate (Copaxone) therapy for multiple sclerosis", Pharmacol Ther., 98:245-255,, 2003.
Dhib-Jalbut, "Mechanisms of action of interferons and glatiramer acetate in multiple sclerosis", Neurology, 25 58(Suppl 4):S3-S9, 2002.
Diabetes Mellitus—Merck Manual, from http://www.merckmanuals.com/professional/print!endocrine_and_metabolic_disorders/diab . . . , pp. 1-22, accessed Apr. 2, 2013.
DMSO Facts, from http://www.theundergroundcure.com/dmso-facts.html, p. 1, accessed Nov. 26, 2014.
Engeloch et al: "Stability of Screening Compounds in Wet DMSO", Journal of Biomolecular Screening, 2008, 13, pp. 999-1006.
European Search Report for EP Appl. No. EP 12180169.0 dated Oct. 25, 2012.
Fleming and Carrithers, "Diagnosis and management of multiple sclerosis", Professional communications, Inc., 4 pages, 2002.
Geary et al., "Pancreatic Glucagon Fails to Inhibit Sham Feeding in the Rat", Peptides, vol. 1, 163-166, 1982.
Glossary of medical education terms, Institute of International Medical Education. http://www.iime.org/glossary.htm. Accessed in Mar. 2013.
Griebel et al.: "SL651498, a GABAA Receptor Agonist with Subtype-Selective Efficacy, as a Potential Treatment for Generalized Anxiety Disorder and Muscle Spasms," CNS Drug Reviews, vol. p, No. 1, pp. 3-20, 2003.
Guideline on clinical investigation of medicinal products for the treatment of multiple sclerosis EMEA, London Sep. 16, 2006.
Human insulin, from http://www.ncbi.nlm.nih.gov/protein/AAA59172.1, p. 1, accessed Nov. 26, 2014.

(56) References Cited

OTHER PUBLICATIONS

Hypoglycemia—Merck Manual, from http://web.archive.org/web/20120115004118/http://www.merckmanuals.com/professional/ pp. 1-2, published on May 2007.
Hyrdochloric Acid, from http://peoplesrx.com/hyrodchloric-acid-and-the-bodys-primary-digestant/, pp. 1-2, accessed Jun. 23, 2016.
Iasemidis LD, "Epileptic Seizure Prediction and Control." IEEE Transac Biomed Eng. 50:549-558. 2003.
International Search Report and Written Opinion issued in PCT Application PCT/US2012/062816, dated Jan. 31, 2013.
International Search Report and Written Opinion issued in PCT Application PCT/US2013/048293, dated Aug. 8, 2013.
International Search Report and Written Opinion issued in PCT Application PCT/US2011/044576, dated Dec. 14, 2011.
International Search Report and Written Opinion issued in PCT Application PCT/US2012/028621, dated Aug. 22, 2012.
International Search Report and Written Opinion Issued in PCT Application No. PCT/US2014/015123, dated Apr. 3, 2014.
International Search Report and Written Opinion issued in PCT/US2015/044060, dated Nov. 2, 2015.
International Search Report and Written Opinion issued in PCT/US2015/014756, dated Sep. 25, 2015.
International Search Report and Written Opinion issued in PCT/US2015/023820, dated Jun. 18, 2015.
International Search Report for PCT/US2016/053628, dated Feb. 9, 2017.
Johnson et al., "Extended use of glatiramer acetate (Copaxone) is well tolerated and maintains its clinical effect on multiple sclerosis relapse rate and degree of disability", Neurology, 50:701-708, 1998.
Kansara et al., "Subcutaneous delivery", Drug. Deliv. Technol, 9(6):38-42, 2009.
Knudsen, F Ursin; "Recurrence risk after first febrile seizure and effect of short term diazepam prophylaxis", Archives of Disease in Childhood, vol. 60, 1985 p. 1045-1049.
Lzutsu, Stabilization of Therapeutic Proteins by Chemical and Physical Methods, pp. 287-292, from Therapeutic Proteins Methods and Protocols, Edited by C. Mark Smales and David C. James, published on 2005.
Meyer et al., "Preparation and in vitro characterization of gentamycin-impregnated biodegradable beads suitable for treatment of osteomyelitis", Journal of Pharmaceutical Sciences, 87(9):1149-1154, 1998.
Nash, "Suspensions", Encyclopedia of Pharmaceutical Technology, 6:3597-3610, 2007.
Naturally-occurring amino acids, from http://www.benjamin-mills.com/chemistry/amino-acids.htm pp. 1-5 , accessed Jun. 23, 2016.
Noseworthy et al, "Multiple sclerosis", New Engl. J. Med., 343:938-952, 2000.
Pellock, John et al.: Pediatric Epilepsy: Diagnosis and Therapy: Third Edition—Chapter 19 "Febrile Seizures", 2008, p. 293-301.
Richards et al. "Trehalose: a review of properties, history and human tolerance, and results of multiple safety studies," *Food and Chemical Toxicology* 40: 871-898. 2002.
Rubino, Solubilization of Some Poorly Soluble Drugs by Cosolvents, PhD dissertation, The University of Arizona, 1984.
Ruggiere et al., "Glatiramer acetate in multiple sclerosis: A review", CNS Drug Reviews, 13(2):178-191, 2007.
Shire et al., "Challenges in the development of high protein concentration formulations", J. Pharm. Sci., 93(6):1390-1402, 2004.
Tselis et al., "Glatiramer acetate in the treatment of multiple sclerosis", Neuropsychiatric Dis. Treat. 5Q, 3(2):259-267, 2007.
Vanderweele et al., "Glucagon, Satiety From Feeding and Liver/Pancreatic Interactions," Brain Research Bulletin, 17:539-543 (1986).
Wang, "Lyophilization and development of solid protein pharmaceuticals", Int. J. Pharm., 203(1-2):1-60, 2000.
Water, from http://www.biology-online.org/dictionary/Water, pp. 1-3, accessed Apr. 24, 2014.
Weber et al., "Mechanism of action of glatiramer acetate in treatment of multiple sclerosis", Neurotherapeutics, 4(4):647-653, 2007.
Williams and Polli, "The lyophilization of pharmaceuticals: a literature review", Journal of Parenteral Science and Technology, 38(2), 1984.
Wolinsky et al, "Glatiramer acetate in primary progressive multiple sclerosis: Results of a multinationa, multicener, double-blind, placebo-controlled trial", Ann Neurool, 61:14-24, 2007.
Wolinsky, "The use of glatiramer acetate in the treatment of multiple sclerosis", Adv. Neurol., pp. 273-292, 2006.
Zacharis et al., "Volatile buffers can override the 'pH memory' of subtilisin catalysis in organic media", Proc. Natl. Acad. Sci. USA, 96(4):1201-1205, 1999.
Ziemssen and Schrempf, "Glatiramer acetate: Mechanisms of action in multiple sclerosis", International Rev. of Neurobiol., 79:537-570, 2007.
Daiichi Sankyo, Heavy Metal Detoxicant Japanese Pharmacopoeia Dimercaprol Injection BAL Intramuscular Injection 100 mg "Daiichi Sankyo", $6^{th}$ edition, 2009, p. 1-2.
Edited by Katsuharu Kato, Medical English-Japanese Dictionary, B6 size, $11^{th}$ edition, $3^{rd}$ issue, Nanzando, 2002, p. 1082.
Eisai, Anesthesia Induction Agent, Sairesu intravenous push 2mg appended paper, $7^{th}$ edition, 2009, p. 1-3.
Extended European Search Report issued in European Application No. 17151475.5, dated Sep. 4, 2017.
Fuji Pharma, sustained Corpus Luteum Hormone formulation PROGESTON Depot Intramuscular Injection 125 mg, $4^{th}$ edition, 2009, p. 1-2.
International Preliminary Report on Patentability and Written Opinion issued in International Patent Application No. PCT/US2016/036921, dated Dec. 12, 2017.
International Preliminary Report on Patentability issued in International Application No. PCT/US2016/035792, dated Dec. 14, 2017.
International Preliminary Report on Patentability issued in International Application No. PCT/US2016/053628, dated Jan. 3, 2018.
Nanzando, Medical Dictionary (Deluxe Version), $18^{th}$ edition, $1^{st}$ issue, Nanzando, 1998, p. 1366.
Notice of Reasons for Rejection issued in Japanese Application No. 2015-520527, dated Nov. 30, 2017.
Office Action issued in Australian Application No. 2017200295, dated Nov. 30, 2017.
Office Action issued in European Application No. 15750582.7, dated Feb. 2, 2018.
Office Action issued in Indonesian Patent Application No. P-00201403186, dated Oct. 17, 2017.
Office Action issued in Israeli Application No. 228348, dated Oct. 29, 2017.
Office Action issued in Israeli Application No. 236393, dated Jul. 12, 2017.
Office Action issued in Thai Patent Application No. 140102311, dated Nov. 2, 2017.
Taiyo Yakuhin Kogyo, Minor Tranquilizer Diazepam Injection 10 mg "Taiyo" appended paper, $9^{th}$ edition, 2009, p. 1-2.
Written Opinion issued in International Application No. PCT/US2016/053628, dated Sep. 28, 2017.
Office Action issued in European Application No. 15706976.6, dated Mar. 8, 2018.
Office Action issued in Japanese Patent Application No. 2017-506262, dated Mar. 4, 2019.
Office Action issued in Chinese Patent Application No. 201580018099, dated Jan. 3, 2019.
Office Action issued in Canadian Patent Application No. 2,829,400, dated Mar. 20, 2018.
Office Action issued in Chinese Patent Application No. 201610221799.6, dated May 3, 2018.
Office Action issued in Indian Patent Application No. 3948/DELNP/2014, dated Apr. 26, 2018.
Office Action issued in United Arab Emirates Patent Application No. 960/2013, dated Mar. 12, 2018.
Decision of the Examining Division of the European Patent Office to Refuse European Patent Application No. 15 750 582.7, dated Dec. 16, 2020, 21 pages.

\* cited by examiner

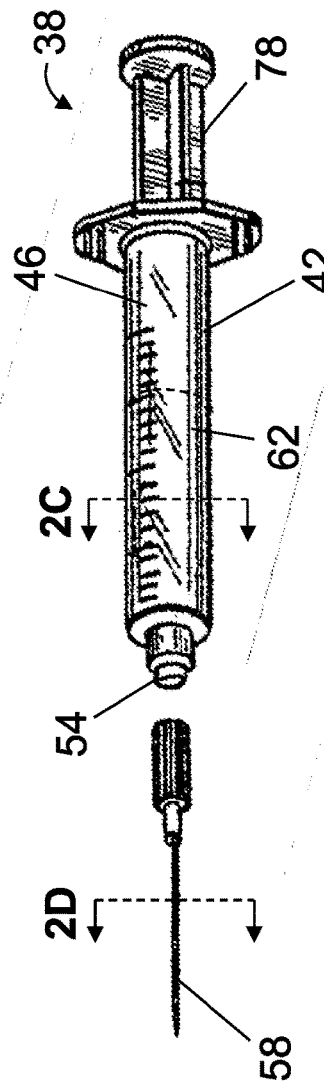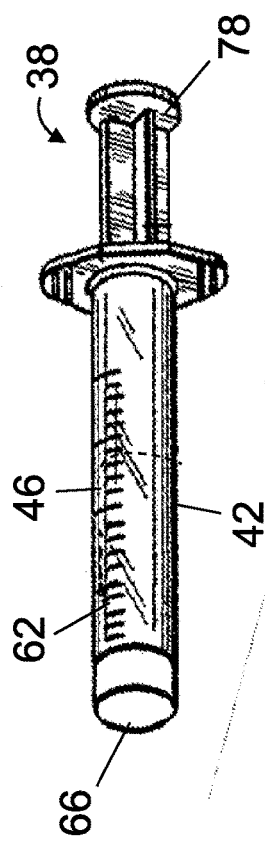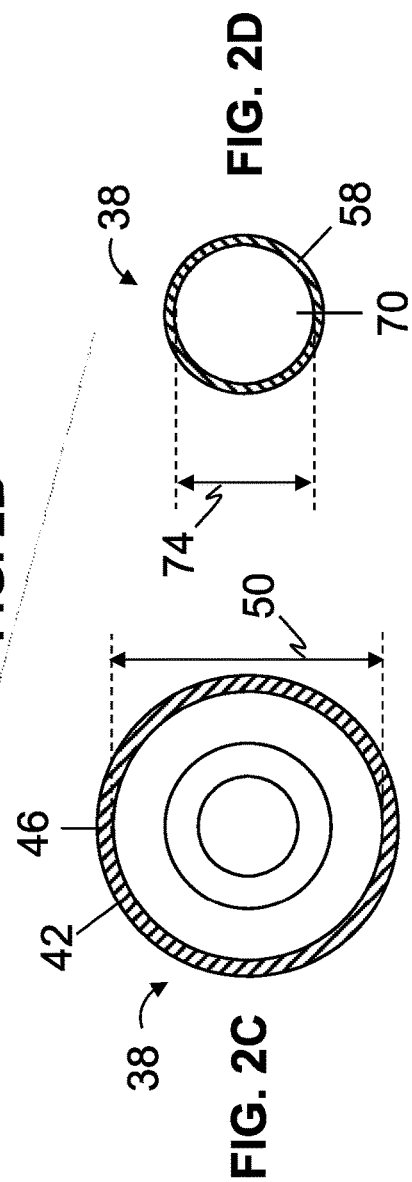

SYRINGES, KITS, AND METHODS FOR INTRACUTANEOUS AND/OR SUBCUTANEOUS INJECTION OF PASTES

This application is a national phase application under 35 U.S.C. § 371 of International Application No. PCT/US2015/044060, filed Aug. 6, 2015, which claims the benefit of priority to U.S. Provisional Patent Application Ser. No. 62/034,004, filed Aug. 6, 2014, the contents of each application is incorporated by reference in its entirety.

BACKGROUND

1. Field of Invention

The present invention relates generally to intracutaneous and/or subcutaneous injection, and more specifically, but not by way of limitation, to intracutaneous and/or subcutaneous injection of pastes.

2. Description of Related Art

A paste, or a two-phase mixture of a solid dispersed in a non-solvent liquid (e.g., relative to the solid), can be an effective structure for delivering medicament(s) (e.g., intracutaneously). For example, pastes may be able to achieve much higher solids concentrations than typical solutions (e.g., water-based solutions) while also providing greater stability relative to aqueous solutions.

Pastes are semisolid dosage forms containing a high percentage of finely dispersed solids (e.g. powder particles) with a stiff consistency. The actual solids content of the paste will primarily depend on the properties of the constituent powder. To prepare a paste, the minimum quantity of fluid that is added to a powder must be sufficient to coat and produce a monolayer of fluid around each individual powder particle. Note that this is an idealized situation where all powder-powder contacts have been fully disrupted, though in reality many micronized powders are highly cohesive and complete disruption of all direct powder-powder contacts may not be possible despite the application of high-shear mixing techniques. Additional fluid is then added to the mixture to fill in the interstitial spaces between the powder particles (i.e. the void volume) and thus enable the particles to flow as a fluid when the yield stress of the paste has been exceeded. Accordingly, powders possessing very low density (i.e. high surface area-to-volume ratio) will require a greater amount of fluid to form a paste compared to powders with a lower surface area-to-volume ratio. Thus, the percent solids content of a paste can vary greatly.

Though being a two-phase system and thus often falling under the category of suspensions, pastes are physically distinct from traditional suspensions in that the concentration of the particulate matter (e.g. powder) in the composition is such that the particles are prevented from settling in the fluid due to steric interactions with neighboring particles. This provides pastes with the stiff consistency, relative to gels, creams, foams and other 'semi-solid' pharmaceutical dosage forms that renders pastes highly viscous.

Accordingly, intracutaneous delivery (e.g., injection) of such pastes may pose difficulties. In particular, such pastes typically have a significantly higher viscosity when compared with traditional aqueous solutions, and it is generally believed that injection of such high viscosity pastes using traditional syringes is difficult, if not impossible (e.g., requiring excessive force and/or causing excessive pain due, for example, the use of large needles). Further, being two-phase mixtures of liquids containing homogeneously dispersed particulate matter, these compositions are particularly susceptible to either partial and/or complete clogging of the delivery device, imposing a further limitation on the potential for intracutaneously delivering therapeutic pastes.

Methods of injecting pastes have been described. For example, U.S. Patent Publication 2006/0211982 describes the preparation of therapeutic pastes for intracutaneous administration. U.S. Patent Publication 2006/0211982 describes paste formulations as typically displaying poor flow properties in standard syringes and that novel needle/syringe designs are required to deliver these formulations. In order to accomplish delivery the injection device preferably incorporates a plunger that can fit into the lumen of the needle, and that acts in a way such that the full amount of the therapeutic formulation loaded into the device is loaded into the lumen of the needle and is then pushed out into the patient upon administration using a positive displacement design. Accordingly, as described in the prior art this type of configuration would require a plunger that fits within the lumen of a needle and is displaced toward the end of the needle upon activation in such a manner that substantially all (e.g., approaching or equal to 100%) of the loaded therapeutic formulation is pushed out of the needle and into the location of injection.

As is well known in the field, commercially available syringes possess internal barrel diameters that are several times larger than the internal diameter of the lumen of a needle. Moreover, the injection device described in the prior art would only be capable of delivering a very small volume of paste and/or fluid through a standard needle. As an example, a typical needle used for subcutaneous injection is a 27-gauge (or 27G), ultra-thin wall (UTW) 6-mm long needle. This needle has an internal diameter of approximately 300 µm (0.300 mm). Modeling the internal volume of the needle as a cylinder of height 6 mm and diameter 0.300 mm, the volume of paste that can be contained within such a needle is $4.24 \times 10^{-4}$ cm$^3$, or approximately 0.42 µL. Typical injection volumes for intracutaneous delivery often range from 100-1000 µL (0.1-1.0 mL), and depending on the indication, drug, etc., the delivered volume may be even larger (e.g. 2000 or 3000 µL). Thus, delivery of most therapeutically relevant volumes will require very long and very large (with respect to the internal diameter) needles.

As further discussed in the prior art, "the needle portion of the injection device is from about 6 to about 8 cm in length, thereby providing a lumen having a sufficient interior volume to contain the dose of semisolid therapeutic formulation and the plunger." U.S. Patent Publication 2006/0211982, paragraph [0115]. Typical needle lengths for intradermal (I.D) and subcutaneous (S.C.) administration are below 0.5 inches (or 1.3 cm). Even deeper intramuscular (I.M.) injections commonly employ needles only between 1.0 and 1.5 inches (or between 2.5-3.8 cm). Accordingly, the needles envisioned for the administration of viscous therapeutic pastes would have to be at least twice as long as commercially available needles. However, even using these long and specially designed needles, and even assuming a relatively large internal diameter, the volume that can be placed within the lumen may still be well below that required to achieve a therapeutic dose. For example, the internal volume of an 8-cm long, 18G needle (internal diameter of 0.84 mm) is only $4.4 \times 10^{-2}$ cm$^3$, or approximately 44 µL.

In addition to the small volumes that can be administered from an arrangement where the entire dose is contained within the lumen of the needle, such long needles typically have to be specially manufactured and may be frightening or repulsive to certain patients due to their length. Moreover, as injection pain can be related to the overall diameter of the needle, such large needles may be very painful, and thus adversely affect patient compliance with a dosing regimen that requires multiple injections with such large needle.

Accordingly, there is a need in the art for compositions, methods, and devices for use in delivering a highly-concentrated, viscous, non-Newtonian fluid comprising a therapeutic (e.g. protein pastes) using standard syringes coupled to needles that are typically used for intracutaneous administration. There is an additional need for compositions, methods, and/or devices for delivery of a volume of a therapeutic paste that may exceed the volume of the lumen of a needle.

SUMMARY

Aspects of the invention described herein are directed to the surprising discovery that high viscosity, non-Newtonian fluids such as pastes (and even high viscosity Newtonian fluids) can be readily delivered from a standard syringe/needle combination. Some embodiments of the present syringes, kits, and/or methods are configured to provide for intracutaneous delivery of pastes. In certain aspects a paste having a solids concentration of greater than 50, 60, 70, 80, 90, or 100 milligrams per mL (mg/mL) is preloaded within a reservoir of a syringe body. Some embodiments of the present syringes, kits, and/or methods are configured, through a Luer fitting disposed on the syringe body configured to releasably secure a needle (e.g., a needle having a size from 18 Gauge to 30 Gauge), to provide for intracutaneous delivery of relativity large volumes (e.g., from 50, 100, or 200 to 1000, 2000, or 3000 μL) of high viscosity pastes using conventional needle sizes. Thus, some embodiments of the present syringes, kits, and/or methods are configured to alleviate the need for custom-made (e.g., single-piece) syringe and needle designs.

Some embodiments of the present pre-loaded syringes comprise a syringe body defining a reservoir, a paste disposed within the reservoir, the paste having a solids concentration of at least about, about, or greater than 50, 60, 70, 80, 90, or 100 mg/mL, a plunger and/or piston disposed within the reservoir and configured to be moved to dispense paste from the reservoir, a Luer fitting disposed on the syringe body and in fluid communication with the reservoir, and a sealing cap disposed on the Luer fitting to seal the reservoir. Some embodiments comprise a needle defining a lumen, the needle configured to be coupled to the syringe body via the Luer fitting to allow intracutaneous delivery of the paste, where the reservoir has an internal first transverse dimension larger than an internal second transverse dimension of the lumen. Embodiments of the present pre-loaded syringes may have the needle affixed to the syringe via a Luer-lock or Luer-slip ("slip-tip") fitting. Alternative embodiments of the present invention may have the needle permanently affixed to the syringe body using, for example, a staked-needle configuration, wherein needle is not removable from the syringe body as with a Luer fitting.

Some embodiments of the present pre-loaded syringes comprise a syringe body defining a reservoir having an internal first transverse dimension, a paste disposed within the reservoir, the paste having a solids concentration of at least about, about, or greater than 50, 60, 70, 80, 90, or 100 mg/mL, a needle defining a lumen having an internal second transverse dimension that is smaller than the first transverse dimension, the needle configured to be in fluid communication with the reservoir to allow intracutaneous delivery of the paste, and a plunger disposed within the reservoir and configured to be moved to dispense paste from the reservoir through the lumen.

In some embodiments of the present pre-loaded syringes, the paste has a volume of between 15, 50, 100, or 500 μL and 1000, 2000, or 3000 μL. In certain aspects the paste can have a volume of between 15 μL and 1000 μL. In some embodiments, the paste has a volume greater than 50 μL. In some embodiments, the paste has a volume greater than 100 μL.

Some embodiments of the present pre-loaded syringes are configured to dispense paste at a flow rate of at least about, about, or greater than 15 microliters per second (μL/s) under a force applied to the plunger having a magnitude of about or at most 50, 60, or 70 newtons (N). In certain aspect the force applied to the plunger can be below 5, 10, 20, 25, 30, 35, 40, 45, 50, 55, 60, 65, or 70 N. In a further aspect the force applied to the plunger can be below 25 N. Some embodiments are configured to dispense paste at a flow rate of greater than 65 μL/s under a force applied to the plunger having a magnitude of about or at most 50 to 70 N.

Some embodiments of the present kits comprise a syringe body defining a reservoir having an internal first transverse dimension and a needle configured to be coupled to the syringe body and defining a lumen having an internal second transverse dimension that is smaller than the first transverse dimension, and a paste having a solids concentration of greater than 50 to 100 mg/mL. In some embodiments, the paste is disposed within the reservoir. In some embodiments, the syringe body comprises a Luer fitting (e.g. Luer-lock or Luer-slip fitting) in communication with the reservoir and a sealing cap disposed on the Luer fitting to seal the reservoir, where the needle is configured to be coupled to the syringe body via the Luer fitting. In some embodiments, the reservoir has a volume of between 50, 75, or 100 μL and 1000, 2000, or 3000 μL.

Some embodiments of the present kits comprise a plunger disposed within the reservoir and configured to be moved to dispense paste from the reservoir through the lumen at a flow rate of greater than 30 μL/s under a force applied to the plunger having a magnitude below 25 N. Some embodiments comprise a plunger disposed within the reservoir and configured to be moved to dispense paste from the reservoir through the lumen at a flow rate of greater than 65 μL/s under a force applied to the plunger having a magnitude below 25 N.

An alternative embodiment is the use of bolus injectors, which are alternatively known as patch pumps or high-volume injectors. In certain aspects a patch pump can be employed for prolonged delivery of viscous pastes to a patient. Examples of these injectors include the SmartDose™ electronic wearable bolus injector (West Pharmaceutical Services, Inc.) and the Lapas bolus injector (Bespak). These devices can be worn on the body and can provide automated intracutaneous delivery of a high concentration paste at a slower infusion rate relative to a traditional auto-injector or manually operated syringe. In these devices the paste is filled in an internal reservoir and slowly infused into the patient at a low volumetric flow rate (relative to manual syringes and auto-injector devices). These devices may be worn like a patch adhered to the skin, delivering the medicament over the course of several minutes, or up to about an hour. As a non-limiting example of the volumetric flow rates that may be employed in these systems, delivery of 3 mL of a therapeutic paste over the course of 10 minutes would entail a delivery rate of 5 μL/second. Delivery of a 3 mL volume of paste over the course of 1 hour would entail a delivery rate of 0.83 μL/second.

Some embodiments of the present methods for intracutaneously injecting a volume of paste comprise moving a plunger of a syringe to dispense paste from a reservoir of the syringe through a lumen of a needle of the syringe, the reservoir having an internal first transverse dimension that is larger than an internal second transverse dimension of the lumen, where the second transverse dimension is between 0.1 and 0.9 mm, where the paste has a solids concentration of greater than 50 to 100 mg/mL, including all values and ranges there between, and where the paste is dispensed at a flow rate of greater than 30 μL/s as the plunger is moved at a rate of between 2 and 50 millimeters per second (mm/s). Some embodiments comprise disposing the needle into and/or through cutaneous tissue of a patient. Some embodiments comprise removing a sealing cap from a Luer fitting of the reservoir. Some embodiments comprise coupling the needle to the reservoir via a Luer fitting disposed on at least one of the needle and the reservoir. In some embodiments, the flow rate of the paste is substantially linearly proportional to the rate of plunger movement.

In some embodiments of the present methods, the injected volume of paste is greater than 10 μL. In some embodiments, the injected volume of paste is between 15, 30, or 100 μL and 1200, 2000, or 3000 μL. In some embodiments, the injected volume of paste is between 30 μL and 100 μL.

In some embodiments of the present syringes, kits, and/or methods, the first transverse dimension is 3 to 16 times larger than the second transverse dimension. In some embodiments, the first transverse dimension is between 1, 2, 3, 4 and 5, 6, 7, 8, 9, 10 mm, including all values and ranges there between. In some embodiments, the second transverse dimension is between 0.1, 0.2, 0.3, or 0.4 and 0.5, 0.6, 07, 0.8, or 0.9 mm, including all values and ranges there between.

In some embodiments of the present syringes, kits, and/or methods, the needle has a size of 18 Gauge or smaller. In some embodiments, the needle has a size of 27 Gauge or smaller. In some embodiments, the needle has a size of 30 Gauge. In some embodiments, the needle has a length smaller than or about 50 mm. In some embodiments, the needle has a length smaller than or about 40 mm. In some embodiments, the needle has a length smaller than or about 13 mm. In some embodiments, the needle has a length of approximately 6 mm.

In some embodiments of the present syringes, kits, and/or methods, the paste has a solids concentration of greater than 200 mg/mL. In some embodiments, the paste has a solids concentration of between 200 and 600 mg/mL. In some embodiments, the paste has a solids concentration of between 300 and 500 mg/mL. In some embodiments, the paste has a solids content of between 1% and 99%. In some embodiments, the paste has a solids content of between 30% and 60%. In some embodiments, the paste has a solids content of between 40% and 50%. In some embodiments, the paste has a density of between 1.0, 1.1, 1.2, 1.3, to 1.4, 1.5, 1.6, 1.7, 1.8, 1.9, 2.0 g/mL, including all values and ranges there between.

As used in this disclosure, a paste is a two-phase mixture of a solid (e.g., a powder containing a medicament and, if necessary, stabilizing excipients) dispersed in a liquid (e.g., a biocompatible diluent), which is a non-solvent to the solid (e.g., and thus, the diluent is typically, but not always, lipophilic in nature). A paste behaves as a solid until a sufficiently large load or stress is applied (typically referred to as the 'yield stress'), at which point the paste flows like a liquid (e.g., pastes may be defined as semi-solids). Pastes may exhibit non-Newtonian fluid behavior, specifically shear-thinning flow characteristics.

The term "coupled" is defined as connected, although not necessarily directly, and not necessarily mechanically; two items that are "coupled" may be unitary with each other.

The terms "a" and "an" are defined as one or more unless this disclosure explicitly requires otherwise.

The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, 10, and 20 percent.

As used herein, the term "intracutaneous injection" encompasses epidermal, intradermal, subcutaneous or intramuscular injection.

As used herein, a "phase" is defined as a homogeneous, physically distinct portion of a system that is separated from other portions of the system by bounding surfaces. It is known that there are three primary phases of matter (solid, liquid and gaseous). As an example, a system containing particulate matter suspended in a liquid that is a non-solvent to the particulate matter is considered a two-phase system. Conversely, a system consisting of organic macromolecules uniformly distributed throughout a liquid such that no apparent boundaries exist between the macromolecules and the liquid molecules is considered a single-phase solution.

As used herein, the term "solids content" reflects the percent mass of solids (e.g. particulate powder) per mass of paste. As an example, a paste of 40% solids content is a two-phase mixture where the solids phase comprises 40% (by mass) of the total paste. A paste of 40% solids content that has an overall density of, for example, 1.2 g/mL would contain mass of solids per milliliter of paste.

As used herein, a "semisolid" is an attribute of a material that exhibits plastic flow behavior. A semisolid material is not pourable, does not readily conform to its container at room temperature, and does not flow at low shear stress. Accordingly, semi-solids have a yield stress that must be exceed before plastic (i.e. non-reversible) deformation occurs.

Accordingly, a semisolid is not a specific physical composition or pharmaceutical dosage form, but rather refers to a physical property of the material. Thus, a variety of materials can be considered semi-solids, as they will possess the attribute of a semi-solid material, despite being physically distinct compositions. For example, the USP-NF describes both a cream and a medicated foam as having a semi-solid consistency, and thus both may be considered semi-solid fluids, or semi-solids, despite being otherwise physically distinct compositions. Similarly, gels and pastes are often both termed semi-solids, despite being physically distinct. Gels are defined by the USP-NF as a dosage form that is a semi-solid dispersion of small particles or a solution of large molecules interpenetrated by a solution containing a gelling agent to provide stiffness. Thus, gels may be either single-phase or two-phase systems. As defined in *Remington: The Science and Practice of Pharmacy* (2006), gel systems may be either clear or turbid, as the ingredients comprising the gel may not be completely soluble or insoluble, or they may form aggregates and disperse light. Gels are defined "as semi-rigid systems in which the movement of the dispersing medium is restricted by an interlacing three-dimensional network of particles or solvated macromolecules in the dispersed phase . . . the interlacing and consequential internal friction is responsible for increased viscosity and the semisolid state."

Gels in which the macromolecules are distributed throughout the liquid in such a manner that no apparent boundaries exist between them and the liquid are called single-phase gels. In instances in which the gel mass consists of floccules of small distinct particles, the gel is classified as a two-phase system and frequently called a magma or a milk. Gels and magmas are considered colloidal dispersions since they each contain particles of colloidal dimension. The generally accepted size range for a substance "colloidal" is when particles fall between 1 nm and 0.5 µm.

By contrast, pastes may be defined as a semisolid dosage form containing a high percentage of finely dispersed solids with a stiff consistency. As discussed earlier, the actual solids content of the paste will primarily depend on the properties of the constituent powder. To prepare a paste, the minimum quantity of fluid that is added to a powder must be sufficient to coat and produce a monolayer of fluid around each individual powder particle. Note that this is an idealized situation where all powder-powder contacts have been fully disrupted, though in reality many micronized powders are highly cohesive, and complete disruption of all direct powder-powder contacts may not be possible, despite the application of high-shear mixing techniques. Additional fluid is then added to the mixture to fill in the interstitial spaces between the powder particles (i.e. the void volume) and thus enable the particles to flow as a fluid when the yield stress of the paste has been exceeded. Accordingly, powders possessing very low density (i.e. high surface area-to-volume ratio) will require a greater amount of fluid to form a paste compared to powders with a lower surface area-to-volume ratio. Thus, gels and pastes may both possess the semi-solid character, and may both be referred to as semi-solids, but they are physically distinct dosage forms. Particularly, the solids concentration of a paste is typically much greater and the particles are often much larger than the upper limit of the colloidal region (0.5 µm). Overall, the USP-NF defines at least six different dosage forms as being semi-solids, including creams, foams, gels, jellies, ointments, and pastes. However, it will be readily known and understood by the skilled technician that these pharmaceutical dosage forms are distinct physical compositions, despite all having the semi-solid attribute and thus broadly termed semisolids.

"Non-Newtonian," as used herein, defines a fluid where the viscosity is dependent on the shear rate or shear rate history. This contrasts with a Newtonian fluid, where the viscosity is typically independent of the applied shear rate.

"Thixotropic," as used herein, defines a fluid that exhibits a shear-thinning property. More specifically, a thixotropic fluid exhibits a time-dependent shear-thinning property, which contrasts with a pseudoplastic fluid, which may characterize a fluid that exhibits time-independent shear-thinning. However, for the purpose of this application, a thixotropic fluid describes shear-thinning fluids in general.

The term "pharmaceutically acceptable" as used herein means suited for normal pharmaceutical applications, i.e. giving rise to no serious adverse events in patients.

The term "pharmaceutically acceptable carrier" means a pharmaceutically acceptable solvent, suspending agent or vehicle for delivering a compound of the present invention to the animal or human. The carrier may be liquid, semisolid or solid.

The term "pharmaceutically acceptable" ingredient, excipient or component is one that is suitable for use with humans and/or animals without undue adverse side effects (such as toxicity, irritation, and allergic response) commensurate with a reasonable benefit/risk ratio.

The term "therapeutic agent" means an agent that effects a desired, beneficial, often pharmacological, effect upon administration to a human or an animal, whether alone or in combination with other pharmaceutical excipients or inert ingredients. In certain aspects of the present invention a therapeutic agent encompasses drugs, vaccines and the like used in the prevention, diagnosis, alleviation, treatment or cure of a condition, ailment or disease.

The term "chemical stability" means that with respect to the therapeutic agent, an acceptable percentage of degradation products produced by chemical pathways such as oxidation or hydrolysis is formed. In particular, a formulation is considered chemically stable if no more than about 20% breakdown products are formed after one year of storage at the intended storage temperature of the product (e.g., 4° C. (refrigerated), or 25° C. (room temperature)); or storage of the product at 30° C./60% relative humidity for one year; or storage of the product at 40° C./75% relative humidity for one month, and preferably three months.

The term "physical stability" means that with respect to the therapeutic agent, an acceptable percentage of aggregates (e.g., dimers, trimers and larger forms) is formed. In particular, a formulation is considered physically stable if no more that about 15% aggregates are formed after one year of storage at the intended storage temperature of the product (e.g., room temperature); or storage of the product at 30° C./60% relative humidity for one year; or storage of the product at 40° C./75% relative humidity for one month, and preferably three months.

The term "stable formulation" means that at least about 65% chemically and physically stable therapeutic agent remains after two months of storage at room temperature. Particularly preferred formulations are those which retain at least about 80% chemically and physically stable therapeutic agent under these conditions.

The term "bioavailability" is defined for purposes of the present invention as the extent to which the therapeutic agent is absorbed from the formulation.

The term "systemic" means, with respect to delivery or administration of a beneficial agent to a subject, that beneficial agent is detectable at a biologically-significant level in the blood plasma of the subject.

The term "slurry" means a thin paste.

The term "controlled-release" is defined for purposes of the present invention as the release of the therapeutic agent at such a rate that blood (e.g., plasma) concentrations are maintained within the therapeutic range but below toxic concentrations over a period of time of about one hour or longer, preferably 12 hours or longer.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 2A is a side-view of one embodiment of the present pre-loaded syringes, showing a removable needle.

FIG. 2B is a side view of the embodiment of FIG. 2A, showing a sealing cap.

FIGS. 2C and 2D are cross-sectional end views of a reservoir and a needle, respectively, of the embodiment of FIG. 2A.

DETAILED DESCRIPTION OF ILLUSTRATIVE EMBODIMENTS

U.S. Pat. No. 8,790,679, to the extent not inconsistent with the present disclosure, is expressly incorporated by reference herein, in its entirety.

Figure 1:
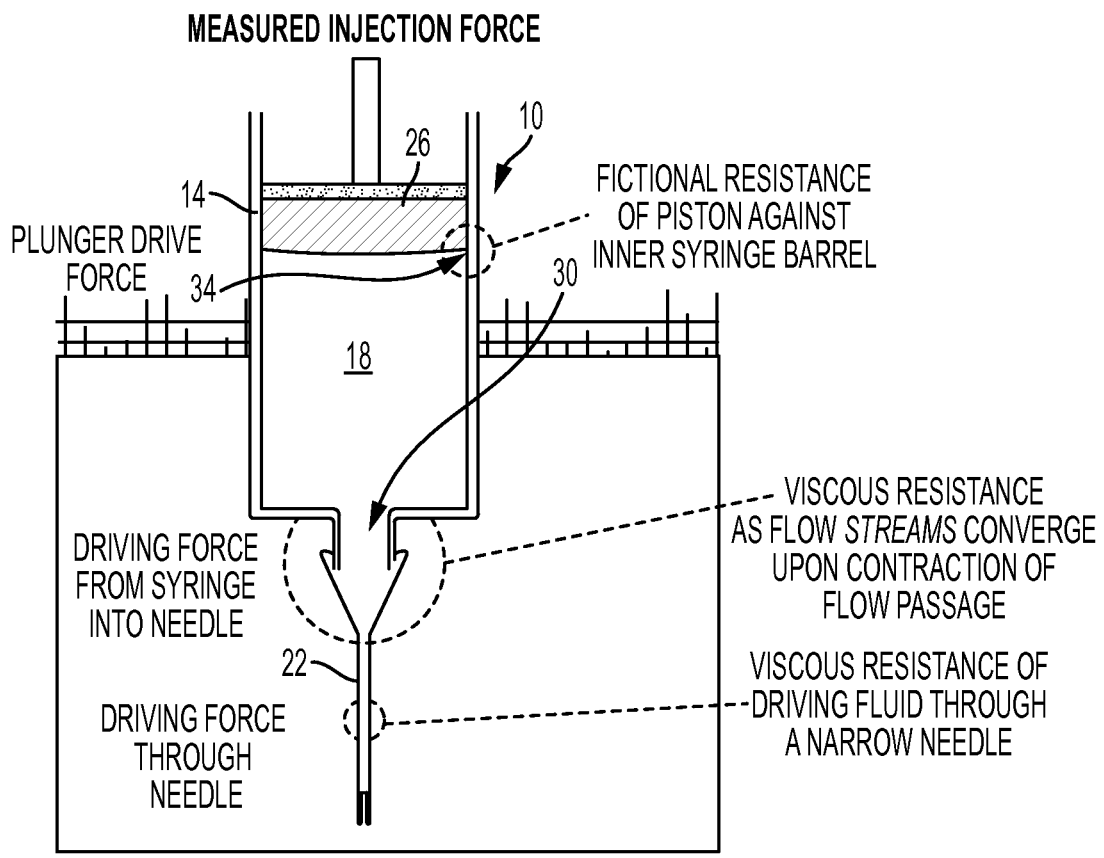
FIG. 1 is a diagram of a conventional syringe, showing various exemplary contributions to injection force.

Referring now to the drawings, and more particularly to FIG. 1, shown is a diagram of a conventional syringe 10, showing various exemplary contributions to injection force (e.g., a force required to cause flow from a syringe, typically applied to a syringe plunger). In this diagram, syringe 10 is shown having a reservoir 14 (containing a substance 18), a needle 22, and a plunger 26. As shown, the total force required to dispense fluid (e.g., including paste, viscous Newtonian and/or non-Newtonian and/or thixotropic fluids, and/or the like) is generally a combination of forces generated within and/or near three particular regions: reservoir exit 30, needle 22, and reservoir/plunger interface 34. For example, at reservoir exit 30, the cross-sectional area through which substance 18 may flow can sharply decrease, which may result in viscous resistance as the substance is forced to flow through reservoir exit 30 and into needle 22. Such viscous resistance can also be present in flow through needle 22 (e.g., which has a relatively small cross-sectional area when compared to reservoir 14). And, in the depicted example, plunger 26 is configured to directly interface with reservoir 14 at reservoir/plunger interface 34 (e.g., a sealed and/or friction fit interface), and frictional forces may occur as plunger is moved relative to reservoir 14. These viscous and/or frictional injection force contributions may be additive to provide the total injection force for a given syringe 10 containing a given substance 18.

Figure 8:
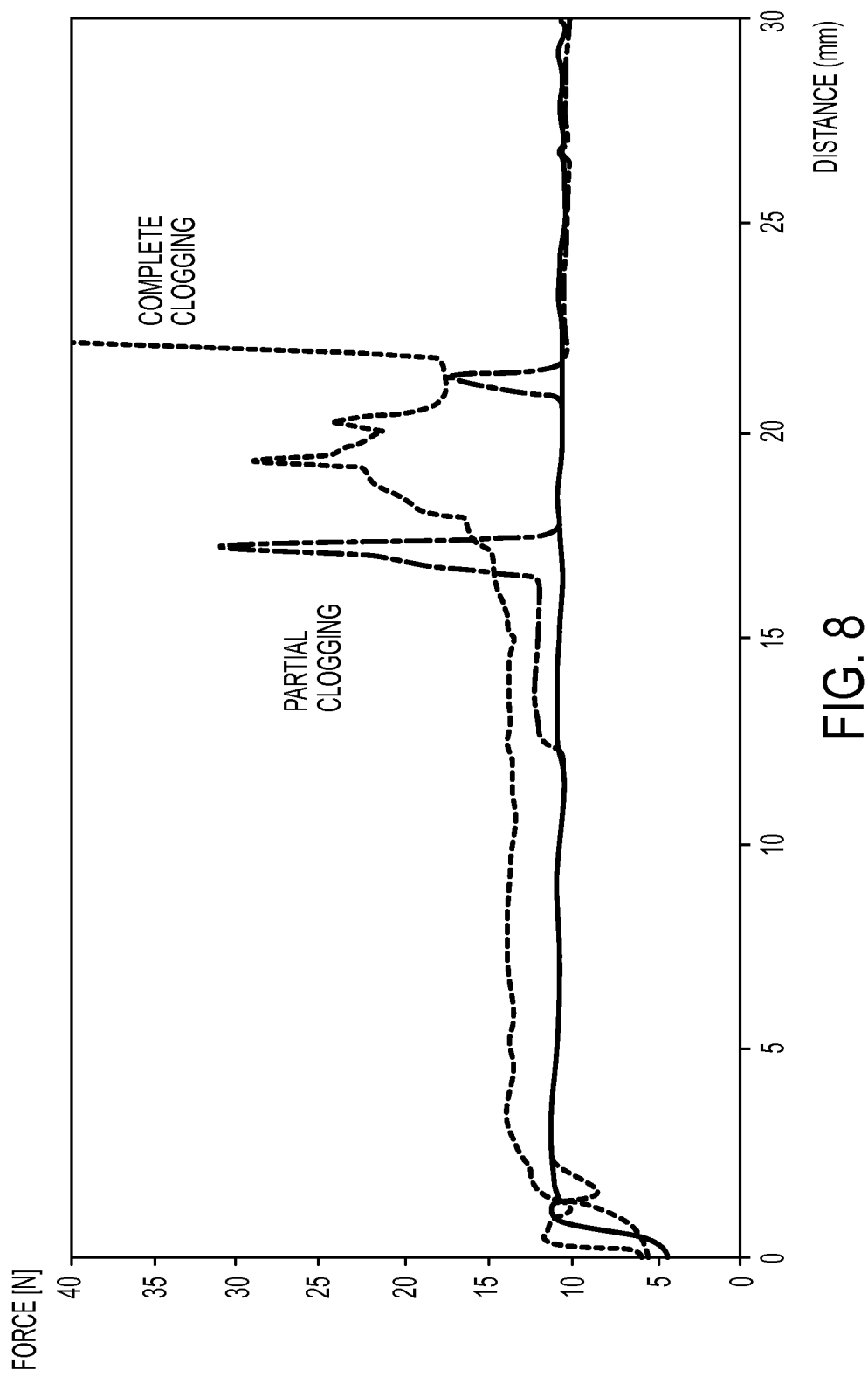
FIG. 8 depict a paste that exhibited both partial and complete clogging while delivered from a 4.6 mm reservoir through a 27G UTW, 6 mm needle at a volumetric flow rate of 33.3 µL/sec.

As will be described below, it may be shown that injection force and/or flow resistance for a given syringe, needle, and/or substance combination can be substantially dominated by viscous effects near a reservoir exit (e.g., 30), for example, due to the sharp change in cross-sectional area proximate this region. Further, it has been observed that in pastes containing cohesive, micronized powders that are highly susceptible to forming robust aggregates (where an aggregate is comprised of two or more powder particles that have not been completely dispersed during mixing) may exhibit partial, and/or complete clogging during delivery of the paste from the syringe reservoir and into the needle. Complete clogging results in the total obstruction of fluid flow from the device. In contrast, partial clogging does not result in the complete obstruction of fluid flow, but may be noted as an abrupt increase in force/pressure during delivery resulting in a discontinuity during fluid delivery. FIG. 8 depicts a paste that exhibited both partial and complete clogging while delivered from a 4.6 mm reservoir through a 27G UTW, 6 mm needle at a volumetric flow rate of 33.3 µL/sec.

FIG. 2A-2D depict a first embodiment of the present pre-loaded syringes, designated by the reference numeral 38. In the embodiment shown, pre-loaded syringe 38 comprises a syringe body 42 defining a reservoir 46 having an internal first transverse dimension (e.g., diameter) 50. In this embodiment, reservoir 46 comprises a substantially circular cross-section; however, in other embodiments, reservoir 46 can comprise any suitable cross-section, such as, for example, square, rectangular, and/or otherwise polygonal, circular, elliptical, and/or otherwise rounded, and/or the like, and the cross-section need not be constant from one end of the reservoir to the other. Table 1 provides non-limiting examples of dimensions for reservoirs which may be suitable for use in some embodiments of the present syringes.

TABLE 1

Illustrative Reservoir Dimensions Consistent with Some Embodiments of the Present Syringes.

|  | Example 1 | Example 2 | Example 3 | Example 4 |
| --- | --- | --- | --- | --- |
| Reservoir Volume (µL) | 100 | 250 | 500 | 1000 |
| Internal Diameter (mm) | 1.46 | 2.30 | 3.30 | 4.61 |
| Cross-sectional Area (mm$^2$) | 1.67 | 4.15 | 8.55 | 16.69 |

Reservoirs of the present disclosure may have volumes, internal diameters (e.g., first transverse dimension 50), cross-sectional areas, and/or the like, that are less than, between any two of, or greater than any one of any value listed in TABLE 1, above.

In the embodiment shown, syringe 38 comprises a Luer fitting 54 (e.g., disposed on syringe body 42) in fluid communication with reservoir 46. In the depicted embodiment, Luer fitting 54 is configured to allow removable coupling of a needle 58 with syringe body 42, for example, to allow intracutaneous delivery of a paste 62 (described in more detail below) from the reservoir through the needle. In this way, embodiments of the present pre-loaded syringes can be provided without a needle attached to the syringe body and can allow a clinician to select, replace, change, and/or the like needles, as may be desired. In the embodiment shown, syringe 38 comprises a sealing cap 66 configured to seal reservoir 46 (e.g., which can be removably coupled to syringe body 42, for example, via Luer fitting 54). Sealing cap 66 can function to seal the reservoir to prevent inadvertent loss, contamination, and/or the like of paste 62, and can be removed from the reservoir to allow attachment of needle 58. Other embodiments of the present pre-loaded syringes can be provided with a needle 58 attached to syringe body 42, and Luer fitting 54 and sealing cap 66 may be omitted.

In the embodiment shown, needle 58 is configured to be in fluid communication with reservoir 46 to allow intracutaneous delivery of paste 62. In this embodiment, needle 58 defines a lumen 70 having an internal second transverse dimension 74 that is smaller than first transverse dimension 50 of reservoir 46. For example, in this embodiment, first transverse dimension 50 is 3 to 16 times larger than second transverse dimension 74. However, in other embodiments, first transverse dimension 50 can be between any two of or greater than any one of 1.1, 1.2, 1.3, 1.4, 1.5, 2, 2.5, 3, 3.5, 4, 4.5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 times second transverse dimension 74. For further example, in this embodiment, first transverse dimension 50 is between 1 and 5 mm, and second transverse dimension 74 is between 0.1 and 0.9 mm.

In the embodiment shown, needle 58 is a 27 Gauge needle; however in other embodiments, needle 58 can comprise any suitable size, such as, for example, 18 Gauge or smaller (where smaller refers to a needle with a smaller internal diameter, or alternatively, a larger gauge), 27 Gauge or smaller, 30 Gauge or smaller, or sizes larger than 18 Gauge, and can comprise any suitable wall size (e.g., ultra-thin wall, thin wall, regular wall, and/or the like). To illustrate, a 30 Gauge regular wall needle can have approximately the same median internal diameter (e.g., second transverse dimension 74) as a 33 Gauge ultra-thin wall needle. Needles that are 30 Gauge and smaller are typically considered pain-free, as some patients may not experience discomfort (or any sensation) when the cutaneous tissue is pierced. Needles of the present disclosure can comprise any suitable length, such as, for example, smaller than 50 mm, smaller than 40 mm, smaller than 10 mm, approximately 6 mm, 6 mm, and/or any other suitable length. For example, needles of the present disclosure can comprise a length that is greater than any one of or between any two of 1, 2, 3, 4, 5, 6, 7, 8, 9, 10, 15, 20, 25, 30, 35, 40, 45, 50, 75, 100, 125, 150, 175, 200, 250, 300, 350, 400, 450, or larger mm.

In the depicted embodiment, syringe 38 comprises a plunger 78 disposed within reservoir 46 and configured to be moved (e.g., relative to the reservoir) to dispense paste 62 from the reservoir.

In the embodiment shown, paste 62 is disposed within reservoir 46 (e.g., syringe 38 is pre-loaded). The reservoir 46 may be made of any material that is suitable for the intended application and that is compatible with the paste 62. Non-limiting examples of reservoir materials include glass (e.g. borosilicate glass) and plastics (e.g. polypropylene, polycarbonate, polystyrene, etc). As described above, reservoir 46 can comprise any suitable dimensions, and any suitable volume of the reservoir may comprise paste 62. For example, in some embodiments, paste 62 has a volume of between 15 µL and 1000 µL. In some embodiments, the paste can have a volume greater than 50 µL, and in some embodiments, the paste can have a volume greater than 100 µL. In some embodiments, the paste can have a volume greater than 1000 µL, and in some embodiments, the paste can have a volume greater than 2000 µL. A volume of paste 62 disposed within reservoir 46 may sometimes be referred to as an injection volume (e.g., if substantially all of the volume of paste is to be injected and/or dispensed from the syringe).

Pastes suitable for use with the present syringes can comprise any suitable material properties (e.g., solids concentrations, solids content, viscosity profile, density, and/or the like). For example, paste 62 can comprise a solids concentration of greater than 100 mg/mL, greater than 200 mg/mL, or between 300 and 500 mg/mL (e.g., greater than any one of or between any two of 100, 125, 150, 175, 200, 225, 250, 275, 300, 325, 350, 375, 400, 425, 450, 475, 500, or greater mg/mL). For further example, paste 62 can comprise a solids content (e.g., a mass of powder relative to a total mass of the paste) of between 30% and 40% (e.g., 35%) (e.g., greater than any one of, or between any two of 1, 5, 10, 15, 20, 25, 30, 35, 40, 45, 50, 55, 60, 65, 70, 75, 80, 85, 90, 95, 99 or more %). For yet further example, paste 62 can comprise a density of between 1.1 and 1.4 g/mL (e.g., 1.25 g/mL) (e.g., greater than any one of or between any two of 1.0, 1.1, 1.2, 1.3, 1.4, 1.5, 1.6, 1.7, 1.8, 1.9, 2, or larger g/mL).

In certain aspects a suitable paste may be a protein paste having a solids content of 35%, a density of 1.3 g/mL, and a solids concentration of approximately 450 mg/mL. In one example, such a paste can be tested, characterized, or optimized by dispensing the paste from a variety of syringes (e.g., having reservoirs with various first transverse dimensions 50 and/or volumes), each equipped with a 27 Gauge ultra-thin wall needle 58 (e.g., having a second transverse dimension 74 of 0.3 mm).

Flow resistance within a needle 58 (e.g., opposing an injection force) can be dependent on volumetric flow rate of a fluid (e.g., paste 62) through the needle, and this volumetric flow rate can also be equal to the volumetric flow rate of the fluid through a reservoir 46 in communication with the needle (e.g., allowing for conservation of mass). If fluid flow rate is matched for syringes having reservoirs with varying dimensions and/or volumes, but substantially identical needles, the flow resistance within the needle for each syringe can be substantially the same as the flow resistance within the needles of the other syringes, and thus any differences in total injection force amongst the syringes may be dominated by viscous effects near the reservoir exits of the syringes (e.g., 30).

Volumetric flow rate can depend on the cross-sectional area (e.g., first transverse dimension 50) of the reservoir and plunger 78 velocity. Thus, volumetric flow rates between syringes with differing reservoirs may be matched by varying applied plunger velocities amongst the syringes. For example, syringes having reservoirs with smaller internal transverse dimensions (e.g. 100 μL volume reservoirs) can require higher plunger velocities than syringes having reservoirs with larger internal transverse dimensions (e.g. 1000 μL volume reservoirs) to attain a given flow rate. For further example, for four illustrative syringes having reservoirs of varying volumes and internal dimensions, TABLE 2 provides respective plunger velocities required to achieve two particular volumetric flow rates: 33.3 μL/s and 67.0 μL/s.

TABLE 2

Plunger Velocities at Two Illustrative Flow Rates for Reservoirs Consistent with Some Embodiments of the Present Syringes.

| Reservoir Volume (μL) | 33.3 μL/s Plunger Velocity (mm/s) | 67.0 μL/s Plunger Velocity (mm/s) |
| --- | --- | --- |
| 100 | 19.91 | 40.00 |
| 250 | 8.02 | 16.12 |
| 500 | 3.90 | 7.83 |
| 1000 | 2.00 | 4.01 |

As shown, some embodiments of the present syringes (e.g., 38) are configured to dispense paste at a flow rate of greater than 30 μL/s as plunger 78 is moved at a rate of between 2 and 40 mm/s. Also, as shown in the depicted examples, flow rate of paste is substantially linearly proportional to the rate of plunger movement.

Figure 3:
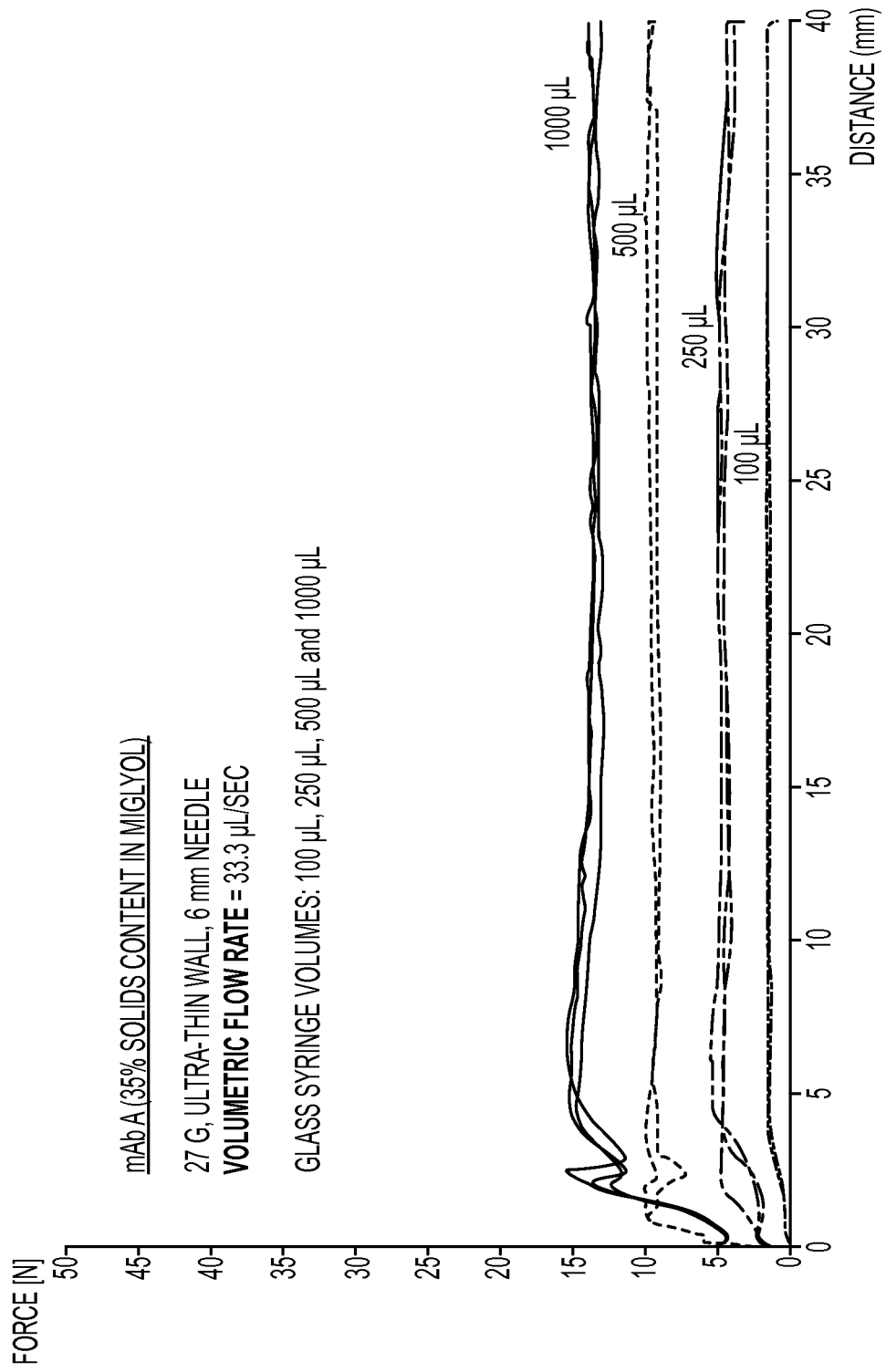
FIG. 3 is a graph of injection force versus plunger movement for various syringe reservoir volumes at first flow rate.
Figure 4:
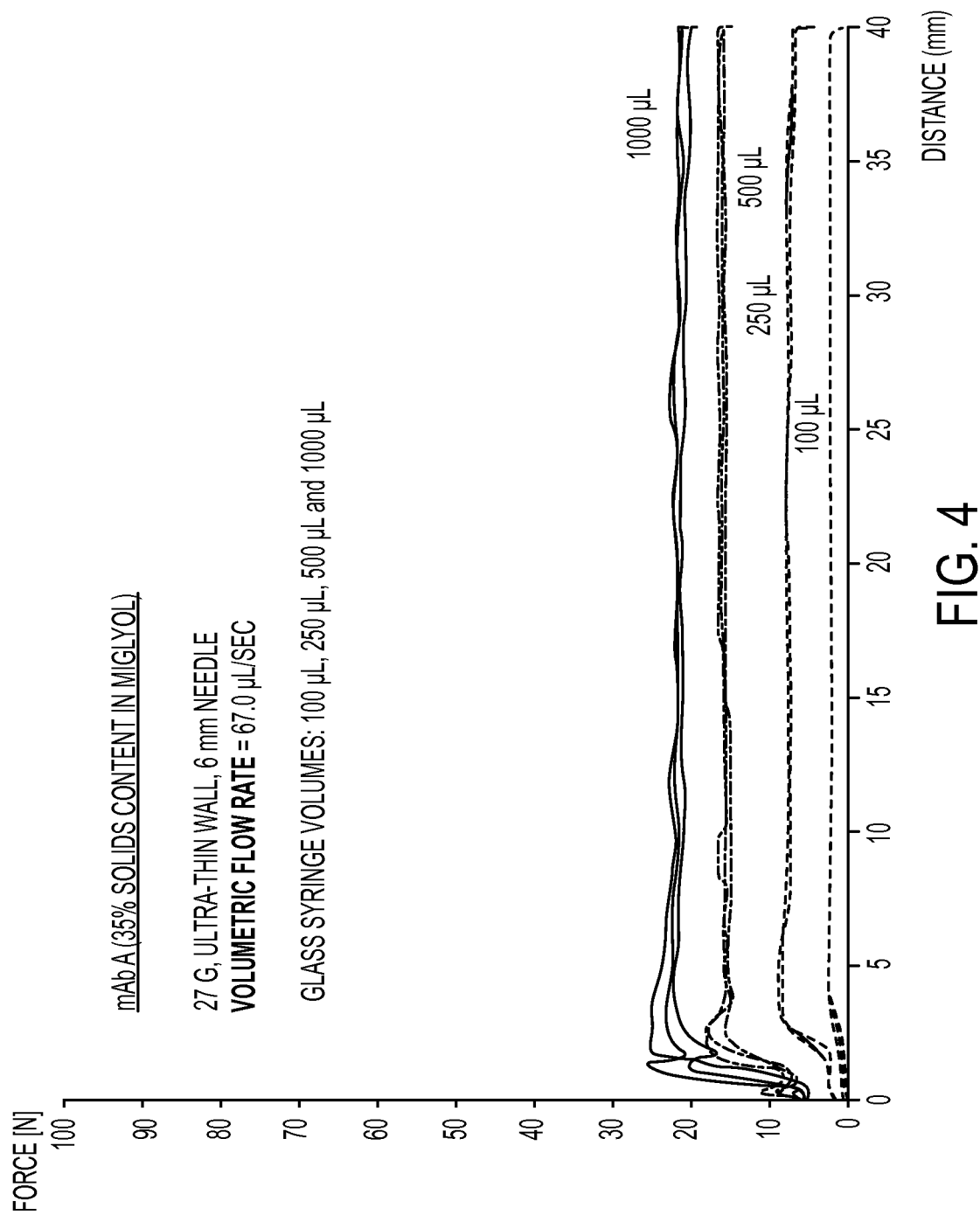
FIG. 4 is a graph of injection force versus plunger movement for various syringe reservoir volumes at a second flow rate.

FIG. 3 and FIG. 4 are graphs that depict injection force (ordinate; units provided in Newtons) versus plunger movement (abscissa; units provided in millimeters) for syringes represented in TABLES 1 and 2, at flow rates represented in TABLE 2. As shown, for a given flow rate, syringes having reservoirs with smaller internal transverse dimensions 50 may produce smoother (e.g., flatter) injection force curves with lower injection force magnitudes than those observed for syringes having reservoirs with larger internal transverse dimensions. One implication of smoother injection force curves is the absence of clogging during paste flow from the reservoir into the needle. As flow rate is increased, syringes having reservoirs with smaller internal transverse dimensions may experience a smaller increase in injection force than syringes with reservoirs with larger internal transverse dimensions. Additionally, syringes having reservoirs with smaller internal transverse dimensions have been noted to be less susceptible to either partial or complete clogging.

Figure 5:
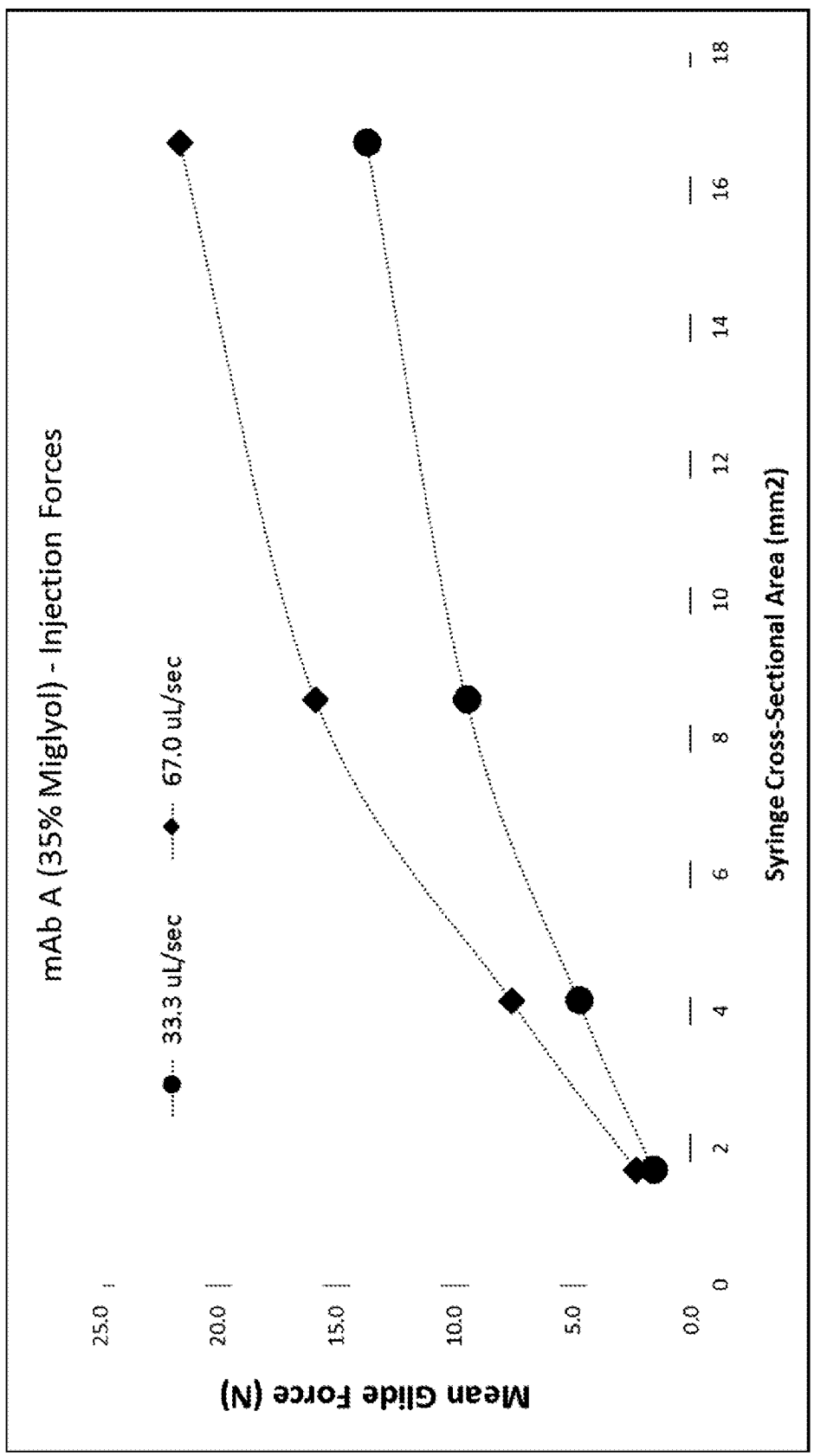
FIG. 5 is a graph of average injection force versus syringe reservoir cross-sectional area at the first and second flow rates.

FIG. 5 is a graph of average injection force versus syringe reservoir cross-sectional area for the syringes represented in TABLES 1 and 2, at the flow rates represented in TABLE 2. As shown, syringes having reservoirs with smaller internal transverse dimensions may require less injection force than syringes having larger internal transverse dimensions at a given flow rate, and/or may be less susceptible to increases in injection force, which may be induced by flow rate increases and/or clog formation.

Figure 6:
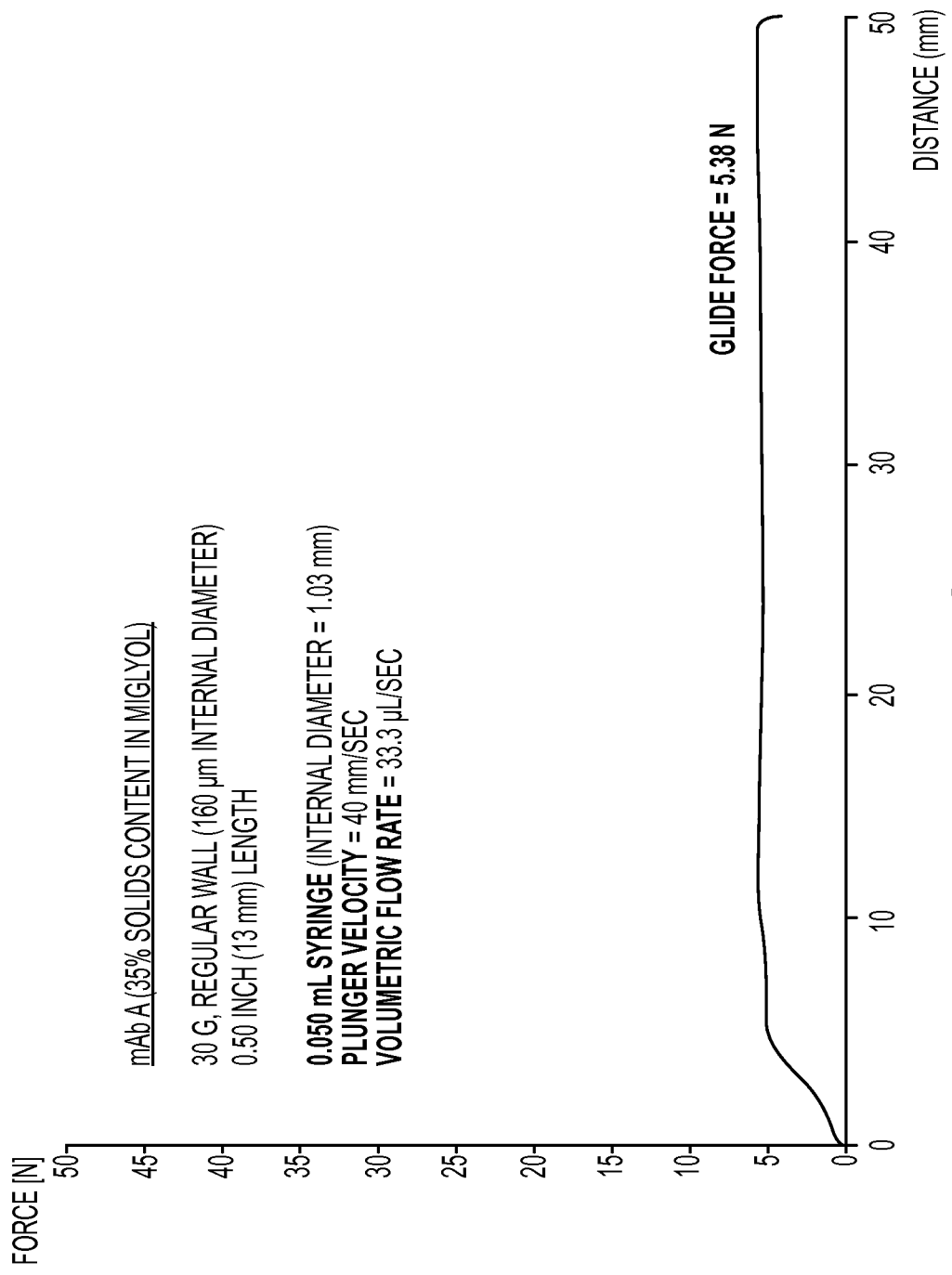
FIG. 6 is a graph of injection force versus plunger movement for a syringe at the first flow rate.

FIG. 6 is a graph of injection forces versus plunger movement for a syringe having a reservoir 46 with a first internal transverse dimension 50 of 1.03 mm, a needle 58 having a lumen 70 with a second internal transverse dimension 74 of 0.160 mm (e.g., a 30 Gauge needle), and a length of 13 mm, at a plunger 78 velocity of 40 mm/s to produce a flow rate of 33.3 μL/s, dispensing the 35% solids content protein paste described above. As shown, the injection force curve is smooth (i.e. free of clog formation), with a magnitude of 5.38 N.

Typically, the upper limit for manual injection force (e.g., considering patient and/or clinician comfort) is approximately 25 N. As shown, some embodiments of the present syringes are configured to dispense paste (e.g., 62) at a flow rate of greater than 30 μL/s under a force (e.g., an injection force) applied to the plunger having a magnitude of below 25 N (e.g., less than 20, 15, 10, or 5 N). Some embodiments are configured to dispense paste at a flow rate of greater than 65 μL/s under a force applied to the plunger having a magnitude below 25 N (e.g., less than 20, 15, 10, or 5 N).

Thus, using embodiments of the present syringes, pastes may be intracutaneously and/or subcutaneously delivered through relatively thin needles (e.g., from 18 Gauge to 30 Gauge, or smaller), using relatively small injection forces (e.g., from 25 N to 5 N, or smaller).

In addition to enabling low injection forces for manual injection, alternative embodiments of the invention enable pastes to be smoothly delivered (i.e. free of partial and/or complete clogging) intracutaneously and/or subcutaneously through relatively thin needles via auto-injectors, where the force driving the plunger/piston is partially or completely provided by an external source (i.e. the energy to displace the piston/plunger and deliver the paste is not provided directly by the patient/clinician). Such an external energy source may be a compressed spring or a compressed gas that drives the piston/plunger of the auto-injector device when the patient activates the device via, for example, the press of a button.

Some embodiments of the present syringes can be configured to provide for any suitable injection force, flow rate, plunger velocity, and/or the like, for example, by varying paste viscosity, solids concentration, solids content, density, and/or the like, needle size, Gauge, length, lumen interior transverse dimension, and/or the like, syringe reservoir size, volume, cross-sectional area, interior transverse dimension, and/or the like.

Figure 7:
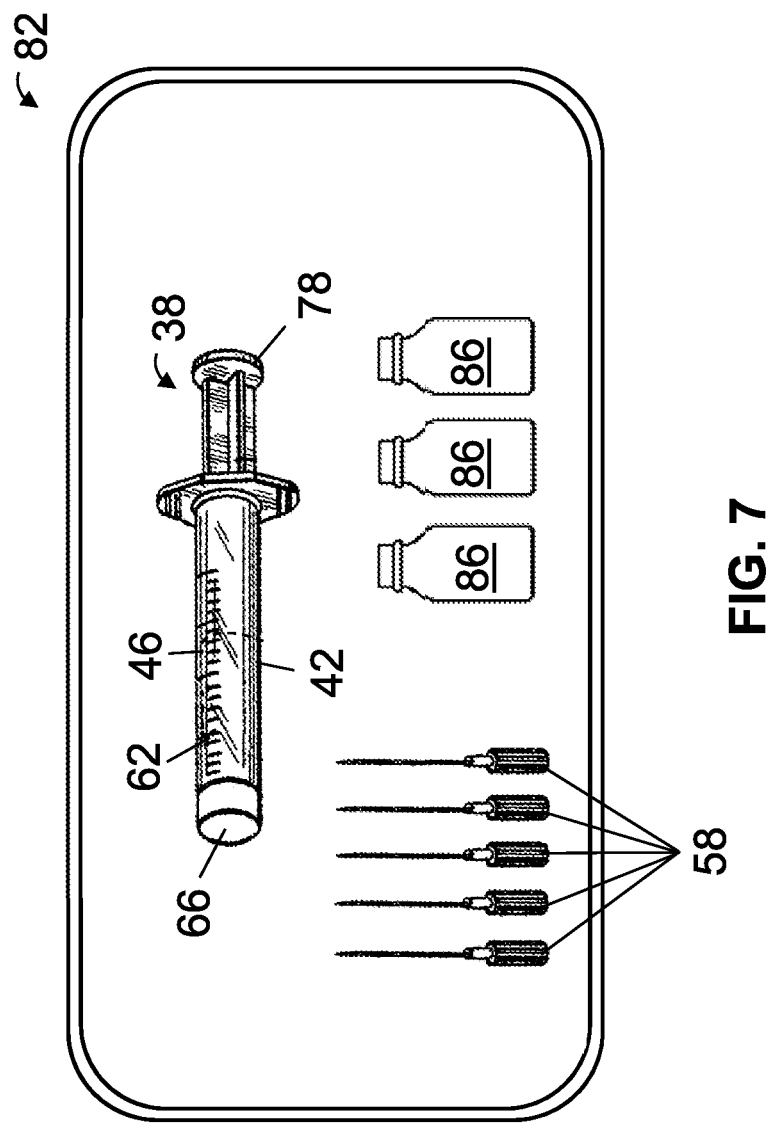
FIG. 7 is a top view of one embodiment of the present kits.

FIG. 7 depicts an embodiment 82 of the present kits. Syringes of the present kits can comprise any and/or all of the features described above for syringe 38. As shown, kit 82 comprises a syringe (e.g., 38), depicted with needle 58 separated from syringe body 42 (e.g., with sealing cap 66 sealing reservoir 46). In the embodiment shown, kit 82 comprises one or more needles (e.g., 58) (e.g., to allow a clinician to select, change, replace, and/or the like needles). In the depicted embodiment, kit 82 comprises one or more containers 86 that can be used to store paste (e.g., 62) (e.g., such that an assembled syringe 38 (e.g., with a needle 58 attached to syringe body 42) can be loaded with paste, for example, by puncturing a seal of a container 86 with the needle and drawing plunger 78 away from syringe body 42). However, in some embodiments, syringe 38 may be preloaded (e.g., as described above).

Some embodiments of the present methods for intracutaneously injecting a volume of paste (e.g., 62) comprise moving a plunger (e.g., 78) of a syringe (e.g., 38) to dispense paste from a reservoir (e.g., 46) of the syringe through a lumen (e.g., 70) of a needle (e.g., 58) of the syringe, the reservoir having an internal first transverse dimension (e.g., 50) that is larger than an internal second transverse dimension (e.g., 74) of the lumen, where the second transverse dimension is between 0.1 and 0.9 mm, where the paste has a solids concentration of greater than 100 mg/L, and where the paste is dispensed at a flow rate of greater than 30 L/s as the plunger is moved at a rate of between 2 and 40 mm/s. Some methods comprise removing a sealing cap (e.g., 66) from a fitting (e.g., a Luer fitting 54) of the reservoir. Some methods comprise coupling the needle to the reservoir via a Luer fitting disposed on at least one of the needle and the reservoir. Some methods comprise disposing the needle into and/or through cutaneous tissue of a patient.

In some methods, the injected volume of paste is greater than 10 µL. In some methods, the injected volume of paste is between 15, 500, or 1000 µL to 1200, 2000, or 3000 µL. In some methods, the injected volume of paste is between 30 µL and 100 µL.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A Spray Dried Powder Containing a Monoclonal Antibody

A spray dried powder containing a monoclonal antibody (where the dried powder contained approximately 70% (w/w) protein) was used to prepare a high-concentration paste formulation by blending the powder with Miglyol 812 to yield a homogeneous two-phase suspension of mAb powder particles dispersed in a non-solvent. The final paste concentration contained 1.6 mL of fluid per gram of powder. As the density of Miglyol at 25° C. is 0.95 g/mL, the solids content of the resulting paste was approximately 40%. The measured density of the paste was 1.12 g/mL and the corresponding solids concentration was 448 mg/mL.

This paste was loaded into glass syringes with varying internal diameters, and delivered through 27G, UTW 6-mm needles (median internal diameter=300 µm) affixed to the syringes via a Luer-lock fitting. The force required to deliver the paste from the syringes was measured using a texture analyzer (force is plotted against the plunger distance).

As shown in the table below, when the same paste is delivered at the same volumetric flow rate through the same needle, the syringe possessing the narrower internal transverse dimension greatly reduces the force required to deliver the concentrated, high-viscosity paste. The lower injection force facilitates delivery and improves the overall ease-of-administration.

The mean injection glide force for N=3 replicates for each syringe are shown in Table 3:

TABLE 3

| Syringe | Plunger Velocity | Flow Rate | Replicate 1 | Replicate 2 | Replicate 3 | Average | StDev |
|---|---|---|---|---|---|---|---|
| 0.50 mL | 7.83 mm/sec | 66.7 µL/sec | 12.15 N | 12.51 N | 12.49 N | 12.38 N | 0.20 N |
| 1.00 mL | 4.01 mm/sec | 66.7 µL/sec | 22.44 N | 22.30 N | 22.58 N | 22.44 N | 0.14 N |

Example 2

A Model Paste Containing Milled Excipient Powder

Figure 9:
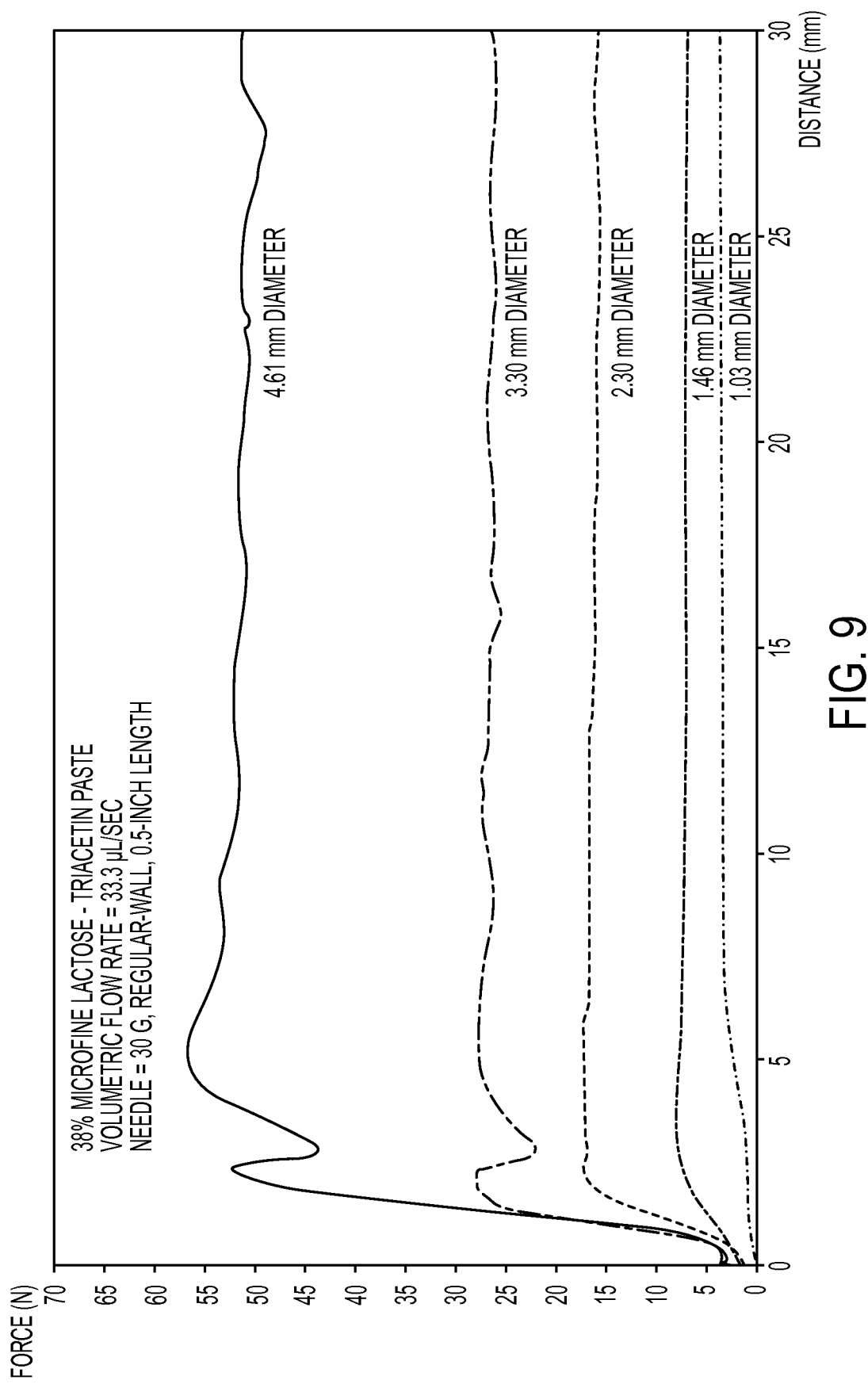
FIG. 9 depicts the force required to deliver the paste from the syringes which was measured using a texture analyzer (where the force required to drive the plunger is plotted against the plunger distance).

A model paste containing only excipient particles was prepared by blending micronized lactose particles ($D_{50} \leq 10$ µm) with triacetin (a triglyceride with viscosity of approximately 18 cP at 25° C.) to prepare a two-phase composition with 38% solids content. The measured density of the paste was 1.24 g/mL and the corresponding solids concentration was approximately 470 mg/mL. The lactose-triacetin paste was loaded into glass syringes with varying internal diameters, and delivered through 30G (30 gauge), regular wall needles (median internal diameter=160 µm) of 0.5 inch length affixed to the syringes via a Luer-lock fitting. The force required to deliver the paste from the syringes was measured using a texture analyzer (where the force required to drive the plunger is plotted against the plunger distance) (FIG. 9).

As shown in the table below, when the same paste is delivered at the same volumetric flow rate through the same needle, syringes possessing a narrower internal transverse dimension greatly reduce the force required to deliver the concentrated, high-viscosity paste. The lower injection force facilitates delivery and improves the overall ease-of-administration.

TABLE 4

| Needle Lumen Diameter | Syringe Barrel Internal Diameter | Plunger Velocity | Volumetric Flow Rate | Replicate 3 |
|---|---|---|---|---|
| 0.160 mm | 1.03 mm | 40.00 mm/sec | 33.3 µL/sec | 3.6 N |
| 0.160 mm | 1.46 mm | 19.91 mm/sec | 33.3 µL/sec | 7.2 N |
| 0.160 mm | 2.30 mm | 8.02 mm/sec | 33.3 µL/sec | 16.2 N |
| 0.160 mm | 3.30 mm | 3.90 mm/sec | 33.3 µL/sec | 26.6 N |
| 0.160 mm | 4.61 mm | 2.00 mm/sec | 33.3 µL/sec | 51.4 N |

Further, the smoothness of the injection force profiles of the lactose-triacetin paste were noted to improve as the internal diameter of the syringe barrel decreased, reflecting a reduced tendency for partial clogging during paste delivery. This feature is particularly important for the delivery of two-phase composition such as pastes, where the particulate matter can render the composition susceptible to partial and/or complete clogging during delivery through narrow internal diameter needles, as the highly cohesive powder particles may not be completely disrupted, despite the application of high-shear mixing techniques. Accordingly, an equally important feature of the disclosed invention is the ability to deliver highly-concentrated two-phase compositions through narrow-internal diameter needles commonly used for intracutaneous injection without the formation of partial and/or complete clogging.

The invention claimed is:

1. A pre-loaded syringe, said syringe pre-loaded with a paste, comprising:
    a syringe body defining a reservoir having an internal first transverse dimension;
    a paste disposed within the reservoir, the paste having a volume of between 15 µL and 2000 µL, a stiff consistency, and a solids concentration of greater than 50 mg/mL;
    a plunger disposed within the reservoir and configured to be moved to dispense paste from the reservoir;
    a Luer fitting disposed on the syringe body and in fluid communication with the reservoir;
    a sealing cap disposed on the Luer fitting to seal the reservoir; and
    a needle defining a lumen having an internal second transverse dimension, the needle configured to be coupled to the syringe body via the Luer fitting to allow intracutaneous delivery of the paste;
    wherein the internal first transverse dimension of the reservoir is 3 to 20 times larger than the internal second transverse dimension of the lumen of the needle; and
    wherein the syringe is configured to dispense the paste at a flow rate of greater than 30 µL/s or greater than 65 µL/s under a force applied to the plunger having a magnitude below 50 N.

2. The pre-loaded syringe of claim 1, wherein the solids concentration of the paste is greater than 100 mg/mL.

3. The pre-loaded syringe of claim 1, where the first transverse dimension is between 1 and 10 mm.

4. The pre-loaded syringe of claim 1, where the second transverse dimension is between 0.1 and 0.9 mm.

5. The pre-loaded syringe of claim 1, where the needle has a size of 18 Gauge, 27 Gauge, 30 Gauge, or smaller.

6. The pre-loaded syringe of claim 1, where the needle has a length smaller than 50 mm, 40 mm, or 13 mm.

7. The pre-loaded syringe of claim 6, where the needle has a length of approximately 6 mm.

8. The pre-loaded syringe of claim 1, where the paste has a volume greater than 50 µL or greater than 100 µL.

9. The pre-loaded syringe of claim 1, where the paste has a solids concentration of greater than 200 mg/mL.

10. The pre-loaded syringe of claim 9, where the paste has a solids concentration of between 300 and 500 mg/mL.

11. The pre-loaded syringe of claim 1, where the paste has a solids content of between 1% and 99%.

12. The pre-loaded syringe of claim 11, where the paste has a solids content of between 30% and 50%.

13. The pre-loaded syringe of claim 1, where the paste has a density of between 1.1 and 1.4 g/mL.

14. A kit comprising:
    the pre-loaded syringe of claim 1, where the paste has a solids concentration of greater than 100 mg/mL.

15. A method of intracutaneously injecting a volume of paste comprising:
    moving the plunger of the pre-loaded syringe of claim 1 to dispense paste from the reservoir of the syringe through the lumen of the needle of the syringe, where the internal first transverse dimension of the reservoir is between 1 and 10 mm and the internal second transverse dimension is between 0.1 and 0.9 mm;
    where the paste has a solids concentration of greater than 100 mg/mL; and
    where the paste is dispensed at a flow rate of greater than 30 µL/s as the plunger is moved at a rate of between 2 and 40 mm/s.

16. The pre-loaded syringe of claim 1, wherein the force applied to the plunger has a magnitude below 25 N.

* * * * *